United States Patent
Fischer et al.

(10) Patent No.: US 6,906,007 B2
(45) Date of Patent: Jun. 14, 2005

(54) PHENYL-SUBSTITUTED 5,6-DIHYDROPYRONE DERIVATIVES FOR USE AS PESTICIDES AND HERBICIDES

(75) Inventors: Reiner Fischer, Monheim (DE); Alan Graff, Leverkusen (DE); Folker Lieb, Leverkusen (DE); Astrid Ullmann, Köln (DE); Axel Trautwein, Bergisch Gladbach (DE); Ralf Wischnat, Köln (DE); Udo Schneider, Leverkusen (DE); Mark Wilhelm Drewes, Langenfeld (DE); Christoph Erdelen, Leichlingen (DE); Peter Dahmen, Neuss (DE); Dieter Feucht, Monheim (DE); Rolf Pontzen, Leichlingen (DE)

(73) Assignee: Bayer CropScience AG, Monheim (DE)

( * ) Notice: Subject to any disclaimer, the term of this patent is extended or adjusted under 35 U.S.C. 154(b) by 66 days.

(21) Appl. No.: 10/311,009

(22) PCT Filed: Jun. 8, 2001

(86) PCT No.: PCT/EP01/06522

§ 371 (c)(1),
(2), (4) Date: May 6, 2003

(87) PCT Pub. No.: WO01/98288

PCT Pub. Date: Dec. 27, 2001

(65) Prior Publication Data

US 2004/0102516 A1 May 27, 2004

(30) Foreign Application Priority Data

Jun. 19, 2000 (DE) .......................................... 100 30 094

(51) Int. Cl.$^7$ .......................... A01N 43/16; C07D 309/30
(52) U.S. Cl. ...................... 504/292; 549/218; 549/292; 504/196
(58) Field of Search ............................... 549/218, 292; 504/196, 292

(56) References Cited

U.S. PATENT DOCUMENTS

| | | | |
|---|---|---|---|
| 3,542,809 A | 11/1970 | Nakanishi et al. | 260/332.2 |
| 5,789,440 A | 8/1998 | Ellsworth et al. | 514/460 |
| 5,840,751 A | 11/1998 | Ellsworth et al. | 514/460 |
| 5,936,128 A | 8/1999 | Ellsworth et al. | 568/67 |
| 5,994,274 A | 11/1999 | Fischer et al. | 504/282 |
| 6,251,830 B1 | 6/2001 | Fischer et al. | 504/251 |
| 6,417,370 B1 | 7/2002 | Lieb et al. | 548/408 |
| 6,469,196 B2 | 10/2002 | Fischer et al. | 560/105 |
| 2002/0022575 A1 | 2/2002 | Fischer et al. | 504/221 |

FOREIGN PATENT DOCUMENTS

WO 94/29268 12/1994

OTHER PUBLICATIONS

Organikum, VEB Deutscher Verlag der Wissenschaften, Berlin (month unavailable) 1990, 18$^{th}$ ed., pp. 501–502, D.7.3.5. Reaktionen mit metallorganischen Verbindungen.
Organikum, VEB Deutscher Verlag der Wissenschaften, Berlin (month unavailable) 1977, pp. 517–519, D.7.1.5. Reaktionen von Carbonsäurederivaten mit Basen.
Organikum, VEB Deutscher Verlag der Wissenschaften, Berlin (month unavailable) 1977, pp. 587–589, D.7.2.6. Esterkondensation.
J. Am. Chem., 93 (month unavailable) 1976, pp. 281–282, Darzens Condensation of α–Halolactones. Glycidic Lactones as Intermediates in Acetogenin Synthesis by J. D. White, J. B. Bremner, M. J. Dimsdale and R. L. Garcea.
Houben–Wege Methoden du Organischen Chemie [Method of Organic Chemistry] vol. 8, (month unavailable) 1952, pp. 467–469.
Organic Preparations and Procedures Int. 7(4), pp. 155–158, (month unavailable) 1975, Synthesis Of Chlorocarbonyl Ketenes by S. Nakanishi and K. Butler.
Tetrahedron Letters, vol. 27, No. 24, pp. 2763–2766, (month unavailable) 1986, Dimethyl Arylmalonates From Cerium (IV) Ammonium Nitrate Promoted Reactions of Dimethyl Malonate with Aromatic Compounds in Methanol by E. Baciocchi, D. Dell'Aira, and R. Ruzziconi.
Arch. Pharm. 309, (month unavailable) 1976, pp. 558–564, Zur Synthese von Kawalactonderivaten by A. M. Chirazi, T. Kappe und Erich Ziegler.
Chem. Ind. 37, Oct. 1985, pp. 730–732, Schiffsfarben—eine Spezialität der seenahen Lackindustrie by H. R. Ungerer.

*Primary Examiner*—Amelia A. Owens
(74) *Attorney, Agent, or Firm*—Richard E.L. Henderson

(57) ABSTRACT

The present invention relates to novel phenyl-substituted 5,6-dihydro-pyrone derivatives of the formula (I)

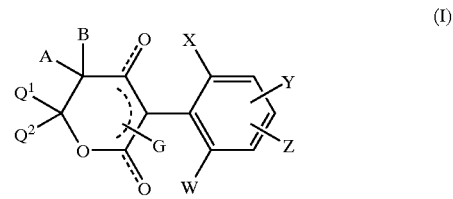

(I)

in which
W, X, Y, Z, G, A, B, $Q^1$ and $Q^2$ are each as defined in the description,
to a plurality of processes for their preparation and to their use as pesticides and herbicides.

8 Claims, No Drawings

PHENYL-SUBSTITUTED 5,6-DIHYDROPYRONE DERIVATIVES FOR USE AS PESTICIDES AND HERBICIDES

The present invention relates to novel phenyl-substituted 5,6-dihydro-pyrone derivatives, to a plurality of processes for their preparation and to their use as pesticides and herbicides.

It is known that certain 5,6-dihydropyrone derivatives have, as protease inhibitors, antiviral properties: WO 95/14012. Furthermore, 4-phenyl-6-(2-phenethyl)-5,6-dihydropyrone is known from the synthesis of kavalactone derivatives: Kappe et al.; Arch. Pharm. 309, 558–64, (1976). Moreover, 5,6-dihydropyrone derivatives are known as intermediates: White, J. D., Brenner, J. B., Deinsdale, M. J., J. Amer. Chem. Soc. 93, 281–2 (1971). Applications in crop protection have hitherto not been described.

This invention now provides novel compounds of the formula (I)

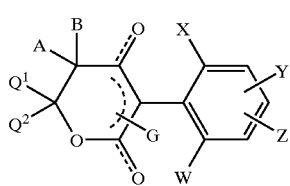

(I)

in which
W represents hydrogen, alkyl, alkenyl, alkinyl, halogen, halogenoalkyl or alkoxy,
X represents halogen, alkyl, alkoxy, alkenyl, alkinyl, halogenoalkyl, halogenoalkoxy, cyano or in each case optionally substituted phenyl, phenoxy, phenylthio, phenylalkoxy or phenylalkylthio,
Y represents hydrogen, alkyl, halogen, halogenoalkyl, alkoxy, alkenyl, alkinyl or optionally substituted aryl or hetaryl,
Z represents hydrogen, halogen, alkyl, alkoxy, halogenoalkyl, halogenoalkoxy or cyano,
A represents a bond, hydrogen, in each case optionally halogen-substituted alkyl, alkenyl, alkoxyalkyl, optionally substituted cycloalkyl or cycloalkylalkyl in which optionally at least one ring atom is replaced by a hetero atom, or in each case optionally halogen-, alkyl-, halogenoalkyl-, alkoxy-, halogenoalkoxy-, cyano- or nitro-substituted aryl, arylalkyl, hetaryl or hetarylalkyl,
B represents hydrogen or alkyl, or
A and B together with the carbon atom to which they are attached represent a saturated or unsaturated unsubstituted or substituted cycle which optionally contains at least one hetero atom, or
B and $Q^1$ together represent alkanediyl which is optionally substituted by in each case optionally substituted alkyl or alkoxy and in which two not directly adjacent carbon atoms optionally form a further optionally substituted cycle or
$Q^1$ represents hydrogen, hydroxyl, alkyl, alkoxy, alkoxyalkyl, alkylacyloxy, optionally substituted cycloalkyl (in which optionally one methylene group is replaced by oxygen or sulphur) or optionally substituted phenyl,
$Q^2$ represents hydrogen or alkyl, or
$Q^1$ and $Q^2$ together with the carbon atom to which they are attached represent an unsubstituted or substituted cycle which optionally contains a hetero atom,
G represents hydrogen (a) or represents one of the groups

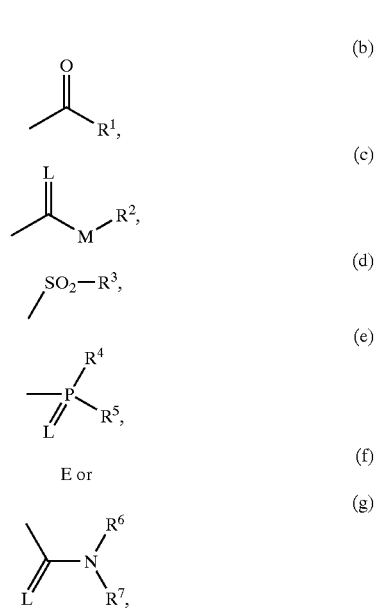

in which
E represents a metal ion or an ammonium ion,
L represents oxygen or sulphur,
M represents oxygen or sulphur,
$R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl in which one or more methylene groups may be replaced by hetero atoms, in each case optionally substituted phenyl, phenylalkyl, hetaryl, phenoxyalkyl or hetaryloxyalkyl,
$R^2$ represents in each case optionally halogen-substituted alkyl, alkenyl, alkoxyalkyl, polyalkoxyalkyl or represents in each case optionally substituted cycloalkyl, phenyl or benzyl,
$R^3$, $R^4$ and $R^5$ independently of one another each represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio, and
$R^6$ and $R^7$ independently of one another each represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a ring which is optionally interrupted by oxygen or sulphur.

Depending inter alia on the nature of the substituents, the compounds of the formula (I) can be present as geometrical and/or optical isomers or isomer mixtures of varying composition which, if required, can be separated in a customary manner. The invention provides both the pure isomers and the isomer mixtures, their preparation and use, and compositions comprising them. Hereinbelow, for the sake of simplicity, only compounds of the formula (I) are referred to, although this may mean both the pure compounds and, if appropriate, also mixtures containing different percentages of isomeric compounds.

Depending on the position of the substituent G, the compounds of the formula (I) can be present in the two isomeric forms of the formulae (I-A) and (I-B)

(I-A)

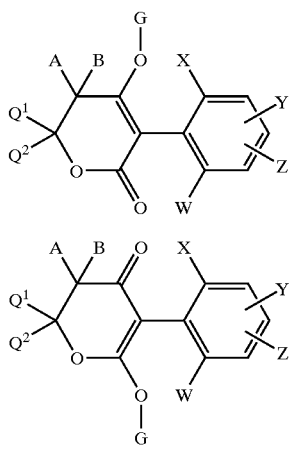

which is meant to be indicated by the broken line in formula (I).

The compounds of the formulae (I-A) and (I-B) can be present either as mixtures or in the form of their pure isomers. Mixtures of the compounds of the formulae (I-A) and (I-B) can, if required, be separated in a manner known per se by physical methods, for example by chromatographic methods.

For reasons of clarity, only one of the possible isomers is shown hereinbelow. This does not exclude that the compounds may, if appropriate, be present in the form of the isomer mixtures or the respective other isomeric form.

Including the different meanings (a), (b), (c), (d), (e), (f) and (g) of group G, the following principal structures (I-a) to (I-g) result:

(I-a):

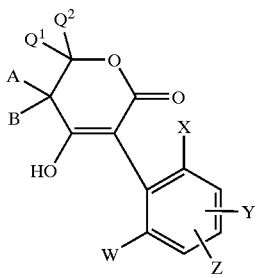

(I-b):

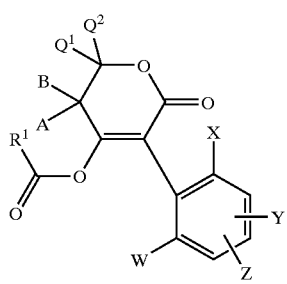

(I-c):

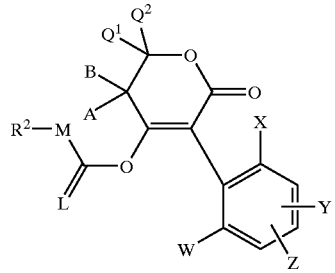

(I-d):

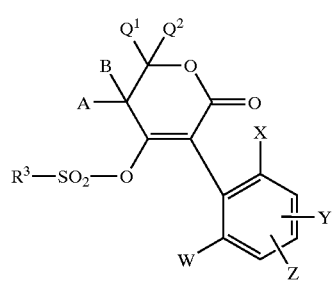

(I-e):

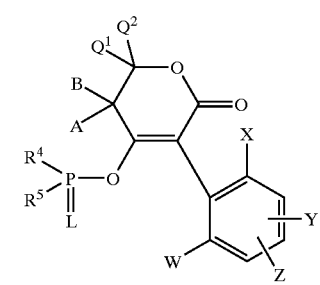

(I-f):

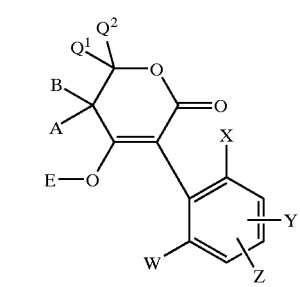

(I-g):

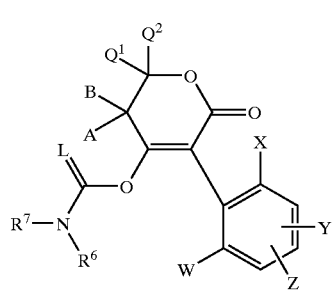

in which
A, B, E, L, M, $Q^1$, $Q^2$, W, X, Y, Z, $R^1$, $R^2$, $R^3$, $R^4$, $R^5$, $R^6$ and $R^7$ are each as defined above.

Furthermore, it has been found that the novel compounds of the formula (I) can be obtained by one of the processes described below:

(A) substituted 5,6-dihydropyrones of the formula (I-a)

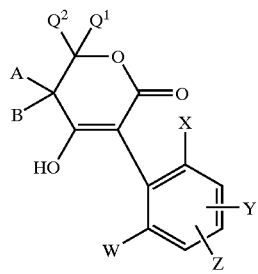

in which

A, B, $Q^1$, $Q^2$, W, X, Y and Z are each as defined above, can be obtained when O-acylhydroxycarboxylic esters of the formula (II)

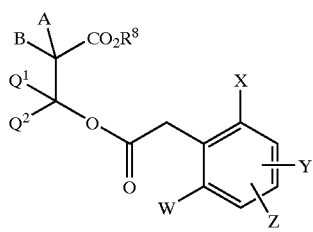

in which

A, B, $Q^1$, $Q^2$, W, X, Y and Z are each as defined above, and $R^8$ represents alkyl (preferably $C_1$–$C_6$-alkyl), are condensed intramolecularly in the presence of a diluent and in the presence of a base.

Furthermore, it has been found (B) that compounds of the formulae (I-a) to (I-g) shown above in which A, B, G, $Q^1$, $Q^2$, W, X, Y and Z are each as defined above are obtained when compounds of the formulae (I-a') to (I-g'), (I-a'):

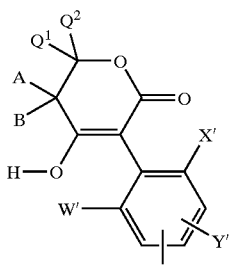

(I-b'):

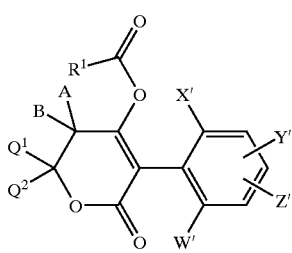

(I-c'):

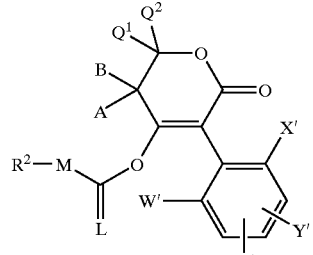

(I-d'):

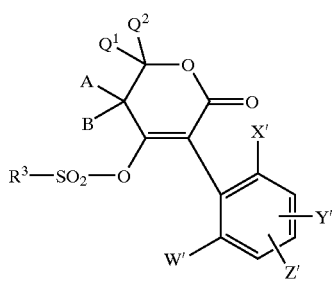

(I-e'):

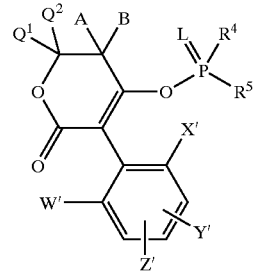

(I-f'):

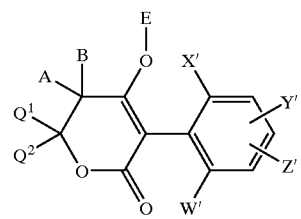

(I-g'):

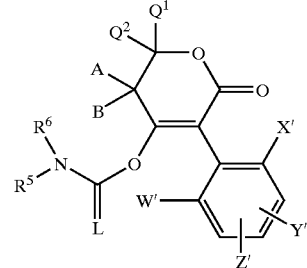

in which

A, B, $R^1$, $R^2$, $R^3$, $R^4$, $R^5$, $R^6$, $R^7$, E, L, M, $Q^1$, $Q^2$, W', X', Y' and Z' each have the meanings of W, X, Y and Z given above and where at least one of the radicals W', X', Y' represents chlorine, bromine or iodine, preferably bromine, and Z' does not represent bromine or iodine, α) are initially reacted with silylacetylene of the formula (III)

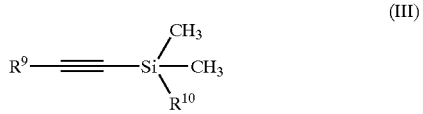 (III)

in which
R⁹ represents hydrogen and
R¹⁰ represents $C_1$–$C_4$-alkyl or phenyl, in particular methyl or tert-butyl,
in the presence of a solvent, a base and a catalyst, suitable catalysts being, in particular, palladium complexes, and the silyl group is subsequently removed, or β) are reacted with vinylstannanes of the formula (IV)

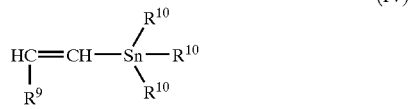 (IV)

in which
R⁹ represents hydrogen, methyl or ethyl and
R¹⁰ represents $C_1$–$C_4$-alkyl, in particular butyl,
in the presence of a solvent, if appropriate in the presence of a base and in the presence of a catalyst, suitable catalysts being, in particular, palladium complexes, or γ) in the specific case where Y' represents chlorine, bromine or iodine, preferably bromine, and W', X' and Z' do not represent bromine or iodine, are reacted with boronic acids of the formula (V)

 (V)

in which
Y represents optionally substituted phenyl or hetaryl,
in the presence of a solvent, a base and a catalyst, suitable catalysts being, in particular, palladium complexes.

Moreover, it has been found
(C) that the compounds of the formula (I-b) shown above in which A, B, Q¹, Q², R¹, W, X, Y and Z are each as defined above are obtained when compounds of the formula (I-a) shown above in which A, B, Q¹, Q², W, X, Y and Z are each as defined above are in each case reacted (α) with acyl halides of the formula (VI)

 (VI)

in which
R¹ is as defined above and
Hal represents halogen (in particular chlorine or bromine)

or (β) with carboxylic anhydrides of the formula (VII)

 (VII)

in which
R¹ is as defined above,
if appropriate in the presence of a diluent and if appropriate in the presence of an acid binder;

(D) that the compounds of the formula (I-c) shown above in which A, B, Q¹, Q², R², M, W, X, Y and Z are each as defined above and L represents oxygen are obtained when the compounds of the formula (I-a) shown above in which A, B, Q¹, Q², W, X, Y and Z are each as defined above are in each case reacted
with chloroformic esters or chloroformic thioesters of the formula (VIII)

 (VIII)

in which
R² and M are each as defined above,
if appropriate in the presence of a diluent and if appropriate in the presence of an acid binder;

(E) that compounds of the formula (I-c) shown above in which A, B, Q¹, Q², R², M, W, X, Y and Z are each as defined above and L represents sulphur are obtained when compounds of the formula (I-a) shown above in which A, B, Q¹, Q², W, X, Y and Z are each as defined above are in each case reacted
with chloromonothioformic esters or chlorodithioformic esters of the formula (IX)

 (IX)

in which
M and R² are each as defined above,
if appropriate in the presence of a diluent and if appropriate in the presence of an acid binder, and (F) that compounds of the formula (I-d) shown above in which A, B, Q¹, Q², R³, W, X, Y and Z are each as defined above are obtained when compounds of the formula (I-a) shown above in which A, B, Q¹, Q², W, X, Y and Z are each as defined above are in each case reacted
with sulphonyl chlorides of the formula (X)

 (X)

in which
R³ is as defined above,
if appropriate in the presence of a diluent and if appropriate in the presence of an acid binder, (G) that compounds of the formula (I-e) shown above in which A, B, L, Q¹, Q², R⁴, R⁵, W, X, Y and Z are each as defined above are obtained when compounds of the formula (I-a) shown above in which A, B, Q¹, Q², W, X, Y and Z are each as defined above are in each case reacted
with phosphorus compounds of the formula (XI)

 (XI)

in which
L, R⁴ and R⁵ are each as defined above and
Hal represents halogen (in particular chlorine or bromine), if appropriate in the presence of a diluent and if appropriate in the presence of an acid binder, (H) that compounds of the formula (I-f) shown above in which A, B, E, $Q^1$, $Q^2$, W, X, Y and Z are each as defined above are obtained when compounds of the formula (I-a) shown above in which A, B, $Q^1$, $Q^2$, W, X, Y and Z are each as defined above are in each case reacted with metal compounds or amines of the formula (XII) or (XIII)

$$Me(OR^{11})_t \quad \text{(XII)}$$

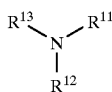
(XIII)

in which

Me represents a mono- or divalent metal (preferably an alkali metal or alkaline earth metal such as lithium, sodium, potassium, magnesium or calcium), t represents the number 1 or 2 and $R^{11}$, $R^{12}$, $R^{13}$ independently of one another each represent hydrogen or alkyl (preferably $C_1$–$C_8$-alkyl), if appropriate in the presence of a diluent, (I) that compounds of the formula (I-g) show above in which A, B, L, $Q^1$, $Q^2$, $R^6$, $R^7$, W, X, Y and Z are each as defined above are obtained when compounds of the formula (I-a) shown above in which A, B, $Q^1$, $Q^2$, W, X, Y and Z are each as defined above are in each case (α) reacted with isocyanates or isothiocyanates of the formula (XIV)

$$R^6\text{—N}=C=L \quad \text{(XIV)}$$

in which $R^6$ and L are each as defined above, if appropriate in the presence of a diluent and if appropriate in the presence of a catalyst or (β) are reacted with carbamoyl chlorides or thiocarbamoyl chlorides of the formula (XV)

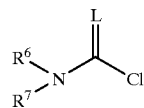
(XV)

in which

L, $R^6$ and $R^7$ are each as defined above, if appropriate in the presence of a diluent and if appropriate in the presence of an acid binder.

Furthermore, it has been found that 5,6-dihydropyrone derivatives of the formula (I) can be prepared by reacting J) silyl enol ethers of the formula

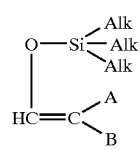
(XVI)

in which

A and B are each as defined above and

Alk represents alkyl having 1 to 4 carbon atoms, in each case with ketene derivatives of the formula

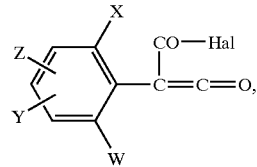
(XVII)

in which

W, X, Y and Z are each as defined above and

Hal represents chlorine or bromine, if appropriate in the presence of a diluent or a diluent mixture and if appropriate in the presence of an acid binder.

Furthermore, it has been found that the novel compounds of the formula (I) have very good activity as pesticides, preferably as insecticides, acaricides and also as herbicides.

The formula (I) provides a general definition of the compounds according to the invention. Preferred substituents or ranges of the radicals listed in the formulae mentioned above and below are illustrated below:

W preferably represents hydrogen, $C_1$–$C_6$-alkyl, $C_2$–$C_4$-alkenyl, ethinyl, fluorine, chlorine, bromine, $C_1$–$C_4$-halogenoalkyl or $C_1$–$C_6$-alkoxy, X preferably represents fluorine, chlorine, bromine, $C_1$–$C_6$-alkyl, $C_1$–$C_4$-halogenoalkyl, $C_1$–$C_6$-alkoxy, $C_2$–$C_4$-alkenyl, ethinyl, $C_1$–$C_4$-halogenoalkoxy, cyano or in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro- or cyano-substituted phenyl or benzyloxy, Y preferably represents hydrogen, $C_1$–$C_6$-alkyl, $C_1$–$C_4$-halogenoalkyl, fluorine, chlorine, bromine, $C_1$–$C_6$-alkoxy, $C_2$–$C_4$-alkenyl, ethinyl or represents one of the radicals

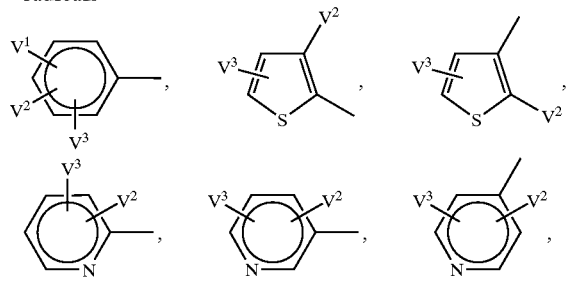

$V^1$ preferably represents hydrogen, halogen, $C_1$–$C_{12}$-alkyl, $C_1$–$C_6$-alkoxy, $C_1$–$C_6$-alkylthio, $C_1$–$C_4$-halogenoalkyl, $C_1$–$C_4$-halogenoalkoxy, nitro, cyano or represents phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, $V^2$ preferably represents hydrogen, fluorine, chlorine, $C_1$–$C_6$-alkyl, $C_1$–$C_6$-alkoxy, $C_1$–$C_4$-halogenoalkyl or $C_1$–$C_4$-halogenoalkoxy, $V^3$ preferably represents hydrogen, fluorine, chlorine, methyl or methoxy, Z preferably represents hydrogen, fluorine, chlorine, bromine, $C_1$–$C_6$-alkyl, $C_1$–$C_4$-halogenoalkyl, $C_1$–$C_6$-alkoxy, $C_1$–$C_4$-halogenoalkoxy or cyano, with the first proviso, that W, X and Z do not represent bromine, $C_2$–$C_4$-alkenyl and ethinyl if Y represents $V^1$-, $V^2$- and $V^3$-substituted phenyl or hetaryl and that secondly only at most two of the radicals W, X and Y represent $C_2$–$C_4$-alkenyl or ethinyl, with the proviso that none of the other radicals W, X, Y and Z may represent bromine, A preferably represents a bond, hydrogen or in each case optionally halogen-substituted $C_1$–$C_{12}$-alkyl, $C_3$–$C_8$-alkenyl, $C_1$–$C_6$-alkoxy-$C_1$–$C_4$-alkyl, in each case optionally halogen-, $C_1$–$C_4$-alkyl- or $C_1$–$C_4$-alkoxy-substituted $C_3$–$C_8$-cycloalkyl or $C_3$–$C_6$-cycloalkyl-$C_1$–$C_4$-alkyl in which optionally one or two not directly adjacent ring members are replaced by oxygen and/or sulphur or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, benzyl, hetaryl having 5 or 6 ring atoms (for example furanyl, pyridyl, imidazolyl, triazolyl, pyrazolyl, pyrimidyl, thiazolyl or thienyl) or hetaryl-$C_1$–$C_4$-alkyl having 5 or 6 ring atoms (for example pyridyl, pyrimidyl or thiazolyl), B preferably represents hydrogen or $C_1$–$C_6$-alkyl, or A, B and the carbon atom to which they are attached preferably represent saturated $C_3$–$C_{10}$-cycloalkyl or unsaturated $C_5$–$C_{10}$-cycloalkyl in which optionally one ring member is replaced by oxygen or sulphur and which are optionally mono- or disubstituted by $C_1$–$C_6$-alkyl, $C_3$–$C_8$-cycloalkyl, $C_1$–$C_6$-halogenoalkyl, $C_1$–$C_6$-alkoxy, $C_1$–$C_6$-alkylthio, halogen or phenyl, with the proviso that $Q^1$ and $Q^2$ do not form a further cycle, or B and $Q^1$ together preferably represent $C_3$–$C_6$-alkanediyl which is optionally mono- or disubstituted by identical or different $C_1$–$C_4$-alkyl and in which two not directly adjacent carbon atoms optionally form a further 3- to 6-membered cycle, or $Q^1$ preferably represents hydrogen, hydroxyl, $C_1$–$C_6$-alkyl, $C_1$–$C_6$-alkoxy, $C_1$–$C_6$-alkoxy-$C_1$–$C_2$-alkyl, $C_1$–$C_6$-alkylacyloxy, optionally fluorine-, chlorine-, $C_1$–$C_4$-alkyl-, $C_1$–$C_2$-halogenoalkyl- or $C_1$–$C_4$-alkoxy-substituted $C_3$–$C_8$-cycloalkyl in which optionally one methylene group is replaced by oxygen or sulphur or optionally halogen, $C_1$–$C_4$-alkyl-, $C_1$–$C_4$-alkoxy-, $C_1$–$C_2$-halogenoalkyl-, $C_1$–$C_2$-halogenoalkoxy-, cyano- or nitro-substituted phenyl, $Q^2$ preferably represents hydrogen or $C_1$–$C_4$-alkyl, or $Q^1$ and $Q^2$ together with the carbon atom to which they are attached preferably represent optionally $C_1$–$C_6$-alkyl-, $C_1$–$C_6$-alkoxy- or $C_1$–$C_2$-halogenoalkyl-substituted $C_3$–$C_7$-cycloalkyl in which optionally one ring member is replaced by oxygen or sulphur, with the proviso that A and B do not form a further cycle, G represents hydrogen (a) or represents one of the groups

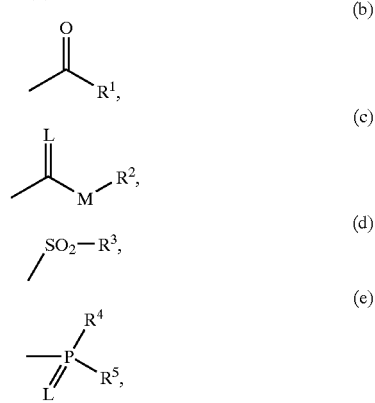

E (f) or

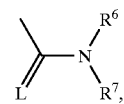

(g)

in particular (a), (b) or (c), in which

E represents a metal ion or an ammonium ion,

L represents oxygen or sulphur and

M represents oxygen or sulphur.

$R^1$ preferably represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl or optionally halogen-, $C_1$–$C_6$-alkyl- or $C_1$–$C_6$-alkoxy-substituted $C_3$–$C_8$-cycloalkyl in which optionally one or more (preferably one or two) not directly adjacent ring members are replaced by oxygen and/or sulphur, or represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, or represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, or represents optionally halogen-, $C_1$–$C_6$-alkyl- or trifluoromethyl-substituted 5- or 6-membered hetaryl (for example pyrazolyl, thiazolyl, pyridyl, pyrimidyl, furanyl or thienyl), or represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl (for example pyridyloxy-$C_1$–$C_6$-alkyl, pyrimidyloxy-$C_1$–$C_6$-alkyl or thiazolyloxy-$C_1$–$C_6$-alkyl), $R^2$ preferably represents in each case optionally halogen-substituted $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, or represents optionally halogen-, $C_1$–$C_6$-alkyl- or $C_1$–$C_6$-alkoxy-substituted $C_3$–$C_8$-cycloalkyl or represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl, $R^3$ preferably represents optionally halogen-substituted $C_1$–$C_8$-alkyl or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^4$ and $R^5$ independently of one another each preferably represent in each case optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio or represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, benzyl, phenoxy or phenylthio, $R^6$ and $R^7$ independently of one another each preferably represent hydrogen, represent in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$- alkyl, represent optionally halogen-, $C_1$–$C_8$-halogenoalkyl-, $C_1$–$C_8$-alkyl- or $C_1$–$C_8$-alkoxy-substituted phenyl, optionally halogen-, $C_1$–$C_8$-alkyl-, $C_1$–$C_8$-halogenoalkyl- or $C_1$–$C_8$-alkoxy-substituted benzyl or together represent an optionally $C_1$–$C_4$-alkyl-substituted $C_3$–$C_6$-alkylene radical in which optionally one carbon atom is replaced by oxygen or sulphur.

In the radical definitions mentioned as being preferred, halogen, also as substituent such as, for example, in halogenoalkyl, represents fluorine, chlorine, bromine and iodine, in particular fluorine and chlorine.

W particularly preferably represents hydrogen, $C_1$–$C_4$-alkyl, chlorine or bromine, X particularly preferably represents chlorine, bromine, $C_1$–$C_4$-alkyl, $C_1$–$C_4$-alkoxy, $C_2$–$C_3$-alkenyl, ethinyl, $C_1$–$C_2$-halogenoalkyl, $C_1$–$C_2$-halogenoalkoxy or cyano, Y particularly preferably represents hydrogen, $C_1$–$C_4$-alkyl, $C_1$–$C_2$-halogenoalkyl, fluorine, chlorine, bromine, $C_1$–$C_4$-alkoxy, $C_2$–$C_3$-alkenyl, ethinyl, 2-thienyl, 3-thienyl or represents the radical

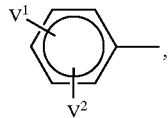

$V^1$ particularly preferably represents hydrogen, fluorine, chlorine, bromine, $C_1$–$C_6$-alkyl, $C_1$–$C_4$-alkoxy, $C_1$–$C_4$-alkylthio, $C_1$–$C_2$-halogenoalkyl, $C_1$–$C_2$-halogenoalkoxy, nitro, cyano or phenyl, $V^2$ particularly preferably represents hydrogen, fluorine, chlorine, $C_1$–$C_4$-alkyl, $C_1$–$C_4$-alkoxy or $C_1$–$C_2$-halogenoalkyl, Z particularly preferably represents hydrogen, fluorine, chlorine, bromine, $C_1$–$C_4$-alkyl, $C_1$–$C_2$-halogenoalkyl, $C_1$–$C_4$-alkoxy or $C_1$–$C_2$-halogenoalkoxy, with the first proviso that W, X and Z do not represent bromine, $C_2$–$C_3$-alkenyl and ethinyl if Y represents $V^1$- and $V^2$-substituted phenyl, 2-thienyl or 3-thienyl and that secondly only one of the radicals X and Y represents $C_2$–$C_3$-alkenyl and ethinyl, with the proviso that in this case none of the other radicals W, X, Y and Z may represent bromine, A particularly preferably represents a bond, hydrogen, in each case optionally fluorine-substituted $C_1$–$C_8$-alkyl, $C_1$–$C_4$-alkoxy-$C_1$–$C_2$-alkyl, in each case optionally fluorine-, chlorine-, methyl-, ethyl- or methoxy-substituted $C_5$–$C_6$-cycloalkyl or $C_3$–$C_6$-cycloalkyl-$C_1$–$C_2$-alkyl in which optionally one ring member is replaced by oxygen or sulphur or in each case optionally fluorine-, chlorine-, bromine-, $C_1$–$C_4$-alkyl-, $C_1$–$C_2$-halogenoalkyl-, $C_1$–$C_4$-alkoxy- or $C_1$–$C_2$-halogenoalkoxy-substituted phenyl or benzyl, B particularly preferably represents hydrogen or $C_1$–$C_4$-alkyl, or A, B and the carbon atom to which they are attached particularly preferably represent saturated $C_5$–$C_7$-cycloalkyl in which optionally one ring member is replaced by oxygen and which is optionally monosubstituted by $C_1$–$C_4$-alkyl, trifluoromethyl or $C_1$–$C_4$-alkoxy, with the proviso that $Q^1$ and $Q^2$ do not form a further cycle, or B and $Q^1$ together particularly preferably represent $C_3$–$C_4$-alkanediyl which is optionally monosubstituted by $C_1$–$C_2$-alkyl and in which two not directly adjacent carbon atoms optionally form a further five- or six-membered cycle, or $Q^1$ particularly preferably represents hydrogen, hydroxyl, $C_1$–$C_4$-alkyl, $C_1$–$C_4$-alkoxy, $C_1$–$C_4$-alkoxy-$C_1$–$C_2$-alkyl, $C_1$–$C_4$-alkylacyloxy or optionally methyl- or methoxy-substituted $C_3$–$C_6$-cycloalkyl in which optionally one methylene group is replaced by oxygen, $Q^2$ particularly preferably represents hydrogen, methyl or ethyl, or $Q^1$ and $Q^2$ particularly preferably together with the carbon to which they are attached represent optionally $C_1$–$C_4$-alkyl-, trifluoromethyl- or $C_1$–$C_4$-alkoxy-substituted saturated $C_5$–$C_6$-cycloalkyl in which optionally one ring member is replaced by oxygen, with the proviso that A and B do not form a further cycle, G particularly preferably represents hydrogen (a) or represents one of the groups (b)

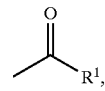

(c)

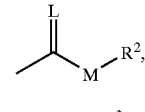

(d)

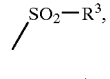

(e)

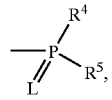

E (f) or (g)

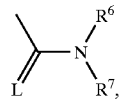

in particular (a), (b) or (c),
in which
E represents a metal ion or an ammonium ion,
L represents oxygen or sulphur and
M represents oxygen or sulphur, $R^1$ particularly preferably represents in each case optionally fluorine- or chlorine-substituted $C_1$–$C_{16}$-alkyl, $C_2$–$C_{16}$-alkenyl, $C_1$–$C_4$-alkoxy-$C_1$–$C_2$-alkyl, $C_1$–$C_4$-alkylthio-$C_1$–$C_2$-alkyl, or optionally fluorine-, chlorine-, $C_1$–$C_2$-alkyl-, or $C_1$–$C_2$-alkoxy-substituted $C_3$–$C_7$-cycloalkyl in which optionally one or two not directly adjacent ring members are replaced by oxygen and/or sulphur, or represents phenyl which is optionally mono- or disubstituted by fluorine, chlorine, bromine, cyano, nitro, $C_1$–$C_4$-alkyl, $C_1$–$C_4$-alkoxy, trifluoromethyl or trifluoromethoxy, or represents pyridyl or thienyl, each of which is optionally monosubstituted by fluorine, chlorine, bromine, methyl, ethyl or trifluoromethyl, $R^2$ particularly preferably represents $C_1$–$C_{16}$-alkyl, $C_2$–$C_{16}$-alkenyl or $C_1$–$C_4$-alkoxy-$C_2$–$C_4$-alkyl, each of which is optionally mono- to trisubstituted by fluorine, or represents $C_3$–$C_7$-cycloalkyl which is optionally monosubstituted by methyl, ethyl or methoxy, or represents phenyl or benzyl, each of which is optionally mono- or disubstituted by fluorine, chlorine bromine, cyano, nitro, $C_1$–$C_4$-alkyl, $C_1$–$C_3$-alkoxy, trifluoromethyl or trifluoromethoxy, $R^3$ particularly preferably represents $C_1$–$C_6$-alkyl which is optionally mono- to pentasubstituted by fluorine or represents phenyl which is optionally mono- or disubstituted by fluorine, chlorine, bromine, $C_1$–$C_4$-alkyl, $C_1$–$C_4$-alkoxy, trifluoromethyl, trifluoromethoxy, cyano or nitro, $R^4$ particularly preferably represents $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, or represents phenyl, benzyl, phenoxy or phenylthio, each of which is optionally mono- or disubstituted by fluorine, chlorine, bromine, nitro, cyano, $C_1$–$C_3$-alkoxy, trifluoromethoxy, $C_1$–$C_3$-alkyl or trifluoromethyl, $R^5$ particularly preferably represents $C_1$–$C_4$-alkyl, $C_1$–$C_4$-alkoxy or $C_1$–$C_4$-alkylthio, $R^6$ particularly preferably represents $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, or represents phenyl which is optionally mono- or disubstituted by fluorine, chlorine, bromine, trifluoromethyl, $C_1$–$C_4$-alkyl or $C_1$–$C_4$-alkoxy, or represents benzyl which is optionally mono- or disubstituted by fluorine, chlorine, bromine, methyl, ethyl, trifluoromethyl or methoxy, $R^7$ particularly preferably represents hydrogen, $C_1$–$C_6$-alkyl or $C_3$–$C_6$-alkenyl, or $R^6$ and $R^7$ together particularly preferably represent a $C_4$–$C_5$-alkylene radical which is optionally mono- or disubstituted by methyl or ethyl and in which optionally one methylene group is replaced by oxygen or sulphur.

In the radical definitions mentioned as being particularly preferred, halogen, also as substituent, such as, for example, in halogenoalkyl, represents fluorine, chlorine, bromine and iodine, in particular fluorine or chlorine, particularly preferably fluorine.

W very particularly preferably represents hydrogen, chlorine, bromine, methyl or ethyl, X very particularly preferably represents chlorine, bromine, methyl, ethyl, n-propyl, methoxy, ethoxy, trifluoromethyl, difluoromethoxy, trifluoromethoxy or cyano (especially chlorine, bromine, methyl, ethyl, n-propyl or trifluoromethyl), Y very particularly preferably represents hydrogen, methyl, ethyl, propyl, iso-propyl, trifluoromethyl, fluorine, chlorine, bromine, methoxy or represents the radical

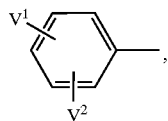

$V^1$ very particularly preferably represents hydrogen, fluorine, chlorine, bromine, methyl, ethyl, iso-propyl, tert-butyl, methoxy, trifluoromethyl or trifluoromethoxy cyano or phenyl, $V^2$ very particularly preferably represents hydrogen, fluorine, chlorine, methyl or trifluoromethyl, Z very particularly preferably represents hydrogen, fluorine, chlorine, bromine, methyl, methoxy or trifluoromethyl (especially hydrogen, fluorine, chlorine, bromine or methyl), with the proviso that W, X and Z do not represent bromine if Y represents $V^1$- and $V^2$-substituted phenyl, A very particularly preferably represents a bond, hydrogen, methyl, ethyl, n-propyl, iso-propyl, n-butyl or iso-butyl, B very particularly preferably represents hydrogen, methyl or ethyl, or A, B and the carbon atoms to which they are attached very particularly preferably represent saturated $C_5$–$C_6$-cycloalkyl in which optionally one ring member is replaced by oxygen and which is optionally monosubstituted by methyl, ethyl, methoxy or ethoxy, with the proviso that $Q^1$ and $Q^2$ do not form a further cycle or B and $Q^1$ together very particularly preferably represent $C_3$–$C_4$-alkanediyl which is optionally monosubstituted by methyl and in which two not directly adjacent carbon atoms optionally form a further three- to six-membered cycle, or $Q^1$ very particularly preferably represents hydrogen, hydroxyl, methyl, ethyl, n-propyl, iso-propyl, methoxy, ethoxy, propoxy, acetyloxy or propionyloxy, $Q^2$ very particularly preferably represents hydrogen, methyl or ethyl, or $Q^1$ and $Q^2$ together with the carbon to which they are attached very particularly preferably represent saturated $C_6$-cycloalkyl which is optionally substituted by methyl, ethyl, methoxy, ethoxy, propoxy or butoxy and in which optionally one ring member is replaced by oxygen, with the proviso that A and B do not form a further cycle, G very particular preferably represents hydrogen (a) or represents one of the groups

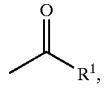
(b)

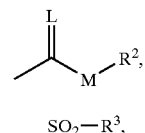
(c)

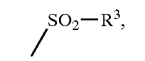
(d)

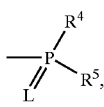
(e)

E (f) or

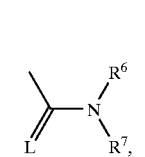
(g)

in particular (a), (b) or (c), in which

E represents a metal ion or an ammonium ion,

L represents oxygen (particularly preferably in the case of (c)) or sulphur and

M represents oxygen or sulphur, $R^1$ very particularly preferably represents in each case optionally fluorine- or chlorine-substituted $C_1$–$C_8$-alkyl, $C_2$–$C_8$-alkenyl, $C_1$–$C_2$-alkoxy-$C_1$-alkyl, $C_1$-alkylthio-$C_1$-alkyl, cyclopropyl, cyclopentyl or cyclohexyl or represents phenyl which is optionally monosubstituted by fluorine, chlorine, bromine, cyano, nitro, methyl, ethyl, iso-propyl, tert-butyl, methoxy, trifluoromethyl or trifluoromethoxy, or represents thienyl or pyridyl, each of which is optionally monosubstituted by chlorine, bromine or methyl, $R^2$ very particularly preferably represents $C_1$–$C_8$-alkyl, $C_2$–$C_8$-alkenyl or $C_1$–$C_4$-alkoxy-$C_2$-alkyl, or cyclohexyl or represents phenyl or benzyl, each of which is optionally monosubstituted by fluorine, chlorine, bromine, cyano, nitro, methyl, tert-butyl, methoxy, trifluoromethyl or trifluoromethoxy, R³ very particularly preferably represents methyl, ethyl, n-propyl, or phenyl which is optionally monosubstituted by fluorine, chlorine, bromine, methyl, tert-butyl, methoxy, trifluoromethyl, trifluoromethoxy, cyano or nitro, R⁴ very particularly preferably represents $C_1$–$C_4$-alkyl, $C_1$–$C_4$-alkoxy, $C_1$–$C_4$-alkylamino, di-($C_1$–$C_4$-alkyl) amino, $C_1$–$C_4$-alkylthio or represents phenyl, phenoxy or phenylthio, each of which is optionally monosubstituted by fluorine, chlorine, bromine, nitro, cyano, $C_1$–$C_2$-alkoxy, trifluoromethoxy or $C_1$–$C_3$-alkyl, R⁵ very particularly preferably represents methyl, ethyl, methoxy, ethoxy, methylthio or ethylthio, R⁶ very particularly preferably represents $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, R⁷ very particularly preferably represents hydrogen, $C_1$–$C_4$-alkyl or $C_3$–$C_4$-alkenyl, or R⁶ and R⁷ together very particularly preferably represent a $C_6$-alkylene radical in which optionally one methylene group is replaced by oxygen or sulphur, W most preferably represents hydrogen, methyl, ethyl, chlorine or bromine, X most preferably represents methyl, ethyl, n-propyl, trifluoromethyl or chlorine, Y most preferably represents methyl, trifluoromethyl, chlorine, bromine, represents phenyl which is optionally mono- or disubstituted by chlorine and/or methyl, Z most preferably represents hydrogen or methyl, with the proviso that W does not represent bromine if Y represents substituted phenyl, A most preferably represents methyl, ethyl or a bond, B most preferably represents methyl or ethyl or A and B and the carbon atom to which they are attached most preferably represent cyclopropyl or cyclohexyl, or B and Q¹ together most preferably represent $C_4$-alkanediyl which is monosubstituted by methyl, Q¹ most preferably represents hydrogen, methyl, methoxy, ethoxy, propoxy, hydroxyl or acetyloxy, Q² most preferably represents hydrogen or methyl, G most preferably represents hydrogen (a) or represents one of the groups

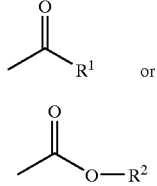

where

R¹ most preferably represents $C_1$–$C_4$-alkyl or represents phenyl or pyridyl, each of which is optionally monosubstituted by chlorine, R² most preferably represents $C_1$–$C_4$-alkyl.

The general or preferred radical definitions or explanations listed above can be combined with one another as desired, i.e. including combinations between the respective ranges and preferred ranges. They apply both to the end products and, correspondingly, to the precursors and intermediates.

Preference according to the invention is given to the compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference according to the invention is given to the compounds of the formula (I) which contain a combination of the meanings listed above as being most preferred.

Saturated or unsaturated hydrocarbon radicals such as alkyl or alkenyl can in each case be straight-chain or branched as far as this is possible, including in combination with hetero atoms, such as, for example, in alkoxy.

Unless indicated otherwise, optionally substituted radicals can be mono- or polysubstituted, and in the case of polysubstitution, the substituents can be identical or different.

Using, according to process (A), ethyl O-[(2,4-dichloro)-phenylacetyl] 1-hydroxy-methyl-cyclohexane-carboxylate as starting material, the course of the process according to the invention can be represented by the following reaction scheme:

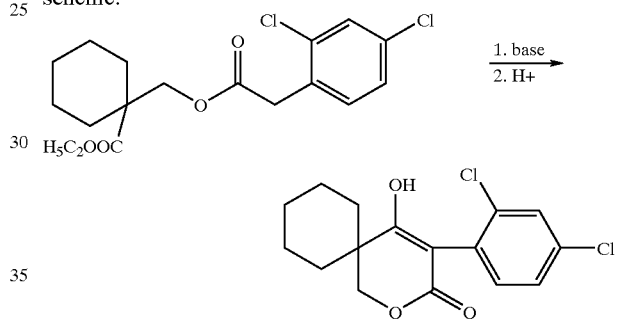

Using, according to process (Bγ), 3-[(2-chloro-4-bromo-6-methyl)-phenyl]-5,5,6,6-tetramethyl-5,6-dihydropyrone and 4-chlorophenylboronic acid as starting materials, the course of the reaction can be represented by the following scheme:

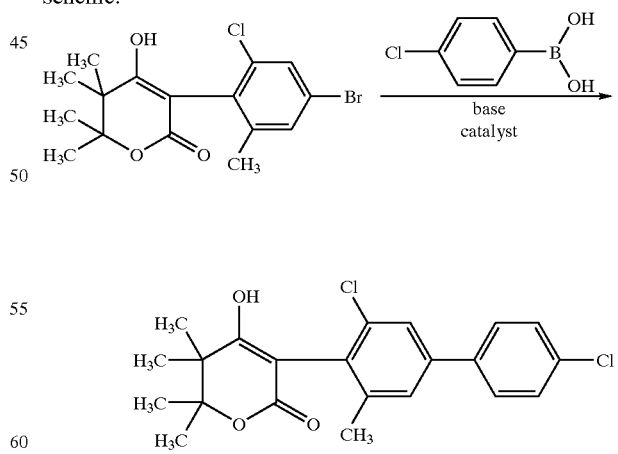

Using, according to process (Cα), 3-[(2,4-dichloro)-phenyl]-5,5,6,6-tetramethyl-5,6-dihydropyrone and pivaloyl chloride as starting materials, the course of the process according to the invention can be represented by the following reaction scheme:

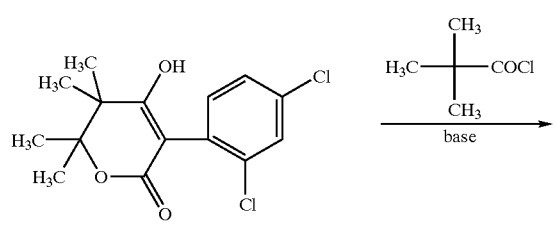

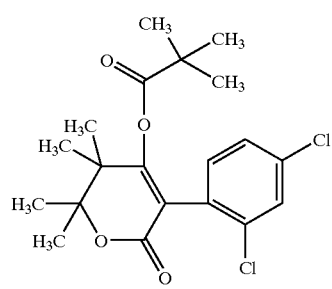

Using, according to process (Cβ), 3-[(4-bromo-2-chloro-6-ethyl)-phenyl]-6,6-dimethyl-5,6-dihydropyrone and acetic anhydride as starting materials, the course of the process according to the invention can be represented by the following reaction scheme:

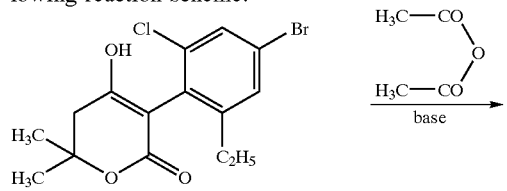

Using, according to process (D), 3-[(2-chloro-6-ethyl-4-phenyl)-phenyl]-5,5-dimethyl-5,6-dihydropyrone and ethoxyethyl chloroformate as starting materials, the course of the process according to the invention can be represented by the following reaction scheme:

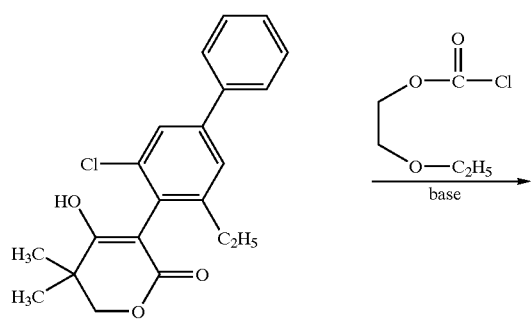

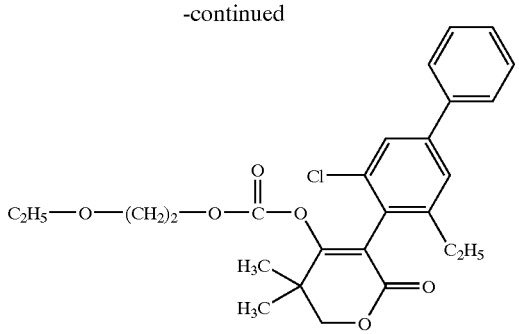

Using, according to process (E), 3-[2,4,6-trichlorophenyl]-5,5,6,6-tetramethyl-5,6-dihydropyrone and methyl chloromonothioformate as starting materials, the course of the reaction can be represented as follows:

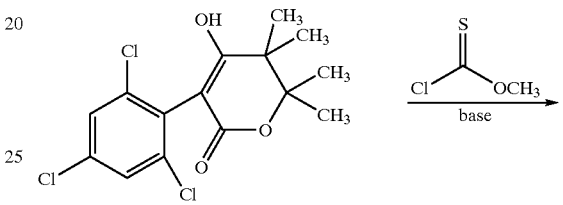

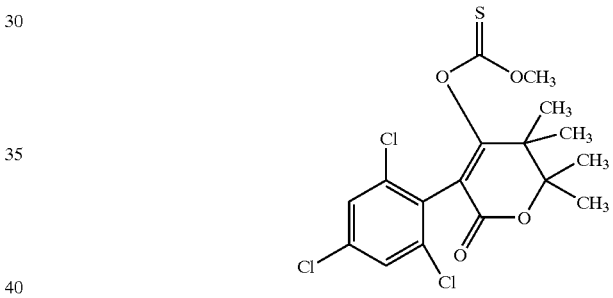

Using, according to process (F), 3-(4-chloro-2-methylphenyl)-5,5-dimethyl-6-methoxy-5,6-dihydropyrone and methanesulphonyl chloride as starting materials, the course of the reaction can be represented by the following reaction scheme:

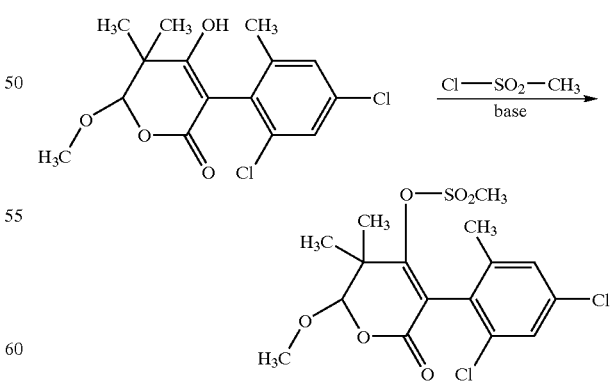

Using, according to process (G), 2-(2-methyl-5-bromophenyl)-5,5,6,6-tetramethyl-5,6-dihydropyrone and 2,2,2-trifluoroethyl methanethio-phosphonate as starting materials, the course of the reaction can be represented by the following reaction scheme:

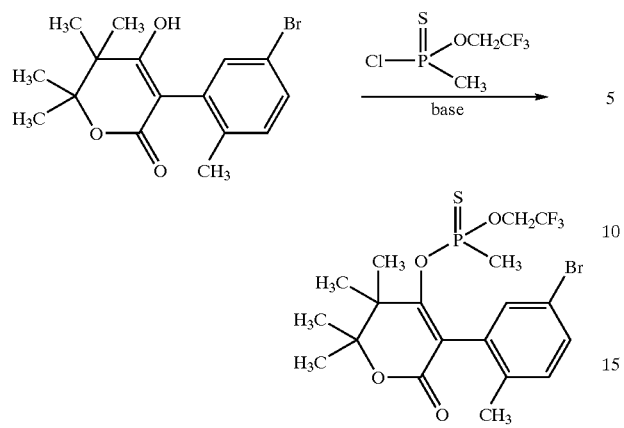

Using, according to process (H), 3-(2,4-dichloro-phenyl)-5,5-pentamethylene-6-methoxy-5,6-dihydropyrone and NaOH as components, the course of the process according to the invention can be represented by the following reaction scheme:

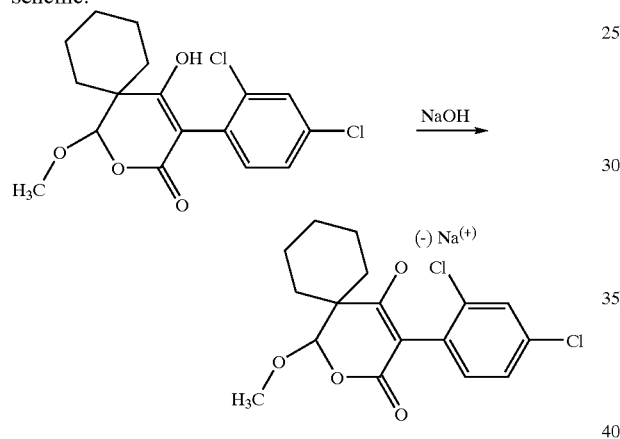

Using, according to process (Iα), 3-(2,4-dichloro-phenyl)-5,5,6,6-tetramethyl-5,6-dihydropyrone and ethyl isocyanate as starting materials, the course of the reaction can be represented by the following reaction scheme:

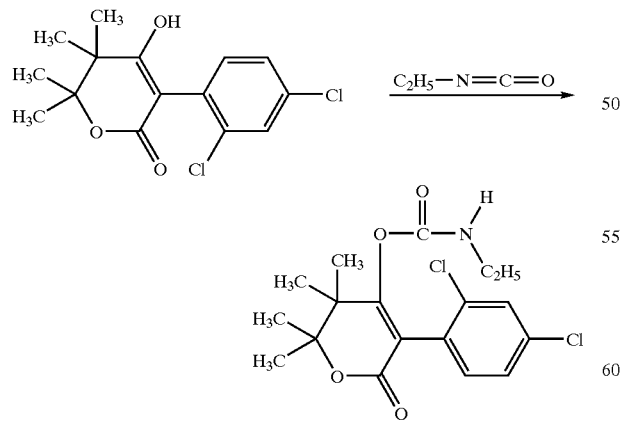

Using, according to process (I•), 3-(2-chloro-4-bromo-phenyl)-5,5-dimethyl-6-methoxy-5,6-dihydropyrone and dimethylcarbamoyl chloride as starting materials, the course of the reaction can be represented by the following scheme:

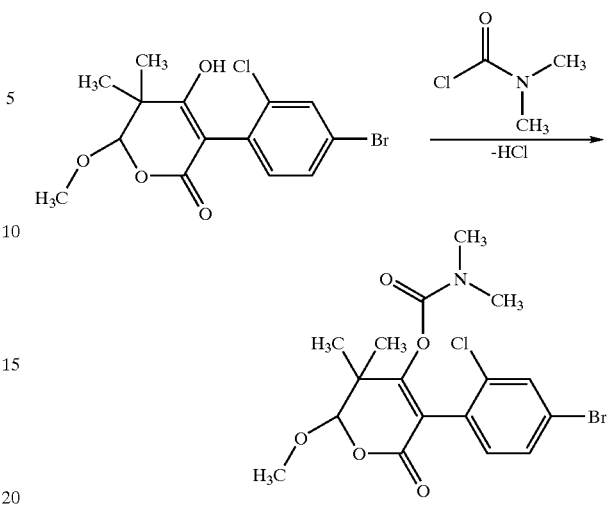

Using chlorocarbonyl 2-mesitylene ketene and trimethyl-silyloxymethylidene-cyclohexane as starting materials, the course of the process (J) according to the invention can be represented by the following formula scheme:

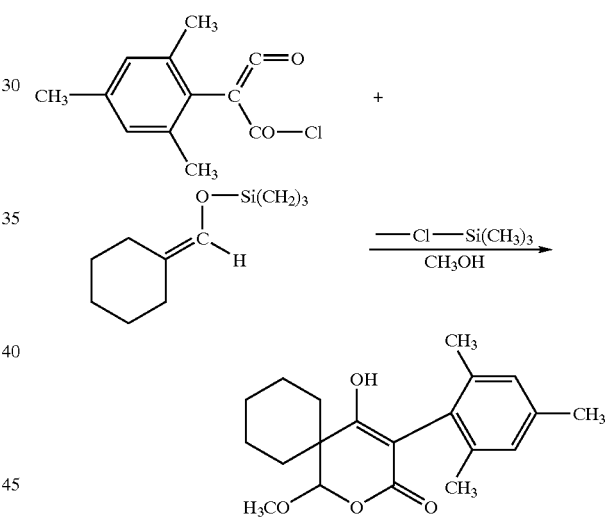

The compounds of the formula (II)

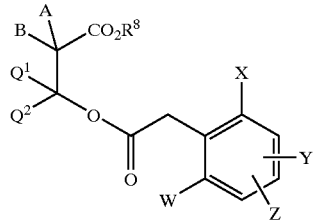

(II)

in which
A, B, $Q^1$, $Q^2$, W X, Y, Z and $R^8$ are each as defined above, required as starting materials in the process (A) according to the invention are novel.

The acylhydroxycarboxylic esters of the formula (II) are obtained, for example, when hydroxycarboxylic esters of the formula (XVIII)

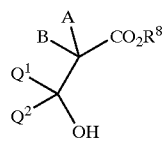

(XVIII)

in which
A, B, $Q^1$, $Q^2$ and $R^8$ are each as defined above,
are acylated with substituted phenylacetyl halides of the formula (XIX)

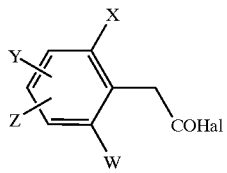

(XIX)

in which
W, X, Y and Z are each as defined above and
Hal represents chlorine or bromine,
(see Preparation Examples for compounds of the formula (II)).

Some of the compounds of the formula (XVIII) are known, or they can be prepared by processes known in principle, for example by Reformatskij synthesis (Organikum, VEB Deutscher Verlag der Wissenschaften, Berlin 1990, $18^{th}$ edition, p. 501 ff.).

Some of the compounds of the formula (XIX) are known and commercially available. They can be prepared by processes known in principle (see, for example, H. Henecka, Houben-Weyl, Methoden der Organischen Chemie [Methods of Organic Chemistry], Vol. 8, pp. 467–469 (1952), WO 97/02243, WO 99/43649).

The compounds of the formula (XIX) are obtained, for example, by reacting substituted phenylacetic acids of the formula (XX)

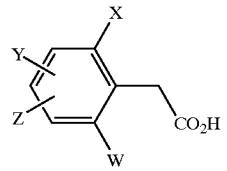

(XX)

in which
W, X, Y and Z are each as defined above,
with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons, such as toluene or methylene chloride), at temperatures of from –20° C. to 150° C., preferably from –10° C. to 100° C.

Some of the compounds of the formula (XX) are commercially available, some are known, or they can be prepared by processes known in principle (for example WO 97/02243, WO 99/43649).

Some of the silylacetylenes of the formula (III) required for carrying out the process B(α) are commercially available, or they can be prepared by generally known processes. Some of the vinylstannanes of the formula (IV) required for carrying out the process B(β) are likewise commercially available, or they can be prepared by known processes.

Some of the boronic acids of the formula (V)

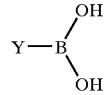

(V)

in which
Y represents optionally substituted phenyl or hetaryl,
required for carrying out the process B(γ) are commercially available, or they can be prepared in a simple manner by generally known processes.

The formula (XVI) provides a general definition of the silyl enol ethers required as starting materials for carrying out the process (J) according to the invention. In this formula, A and B each preferably have those meanings which have already been mentioned in connection with the description of the 5,6-dihydro-pyrones of the formula (I) according to the invention as being preferred for these radicals. Alk preferably represents methyl or ethyl, particularly preferably methyl.

The silyl enol ethers of the formula (XVI) are known or can be prepared by known methods.

The formula (XIV) provides a general definition of the ketene derivatives required as reaction components for carrying out the process according to the invention. In this formula, W, X, Y and Z each preferably have those meanings which have already been mentioned in connection with the description of the 5,6-dihydro-pyrones of the formula (I) according to the invention as being preferred for these radicals. Hal also preferably represents chlorine or bromine.

Ketene derivatives of the formula (XVII) are known or can be prepared by known processes (cf. Org. Prep. Proced. Int. 7, 155–158 (1975) and DE-A 1 945 703). Thus, ketene derivatives of the formula (XVII) are obtained by reacting substituted phenylmalonic acids of the formula (XXI)

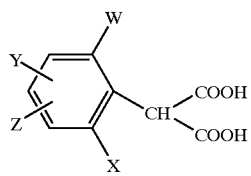

(XXI)

in which
W, X, Y and Z are each as defined above,
with acid halides, such as, for example, thionyl chloride, phosphorus(V) chloride, phosphorus(III) chloride, oxalyl chloride, phosgene or thionyl bromide, if appropriate in the presence of catalysts, such as, for example, diethylformamide, methyl-stearyl-formamide or triphenylphosphine and if appropriate in the presence of bases such as, for example, pyridine or triethylamine, at a temperature between –20° C. and +200° C., preferably between 0° C. and 150° C.

The substituted phenylmalonic acids of the formula (XXI) are known or can be prepared by known methods (cf., for example, Organikum, VEB Deutscher Verlag der Wissenschaften, Berlin 1977, p. 517 ff.). Thus, substituted phenylmalonic acids of the formula (XXI) are obtained by reacting substituted phenylmalonic esters of the formula

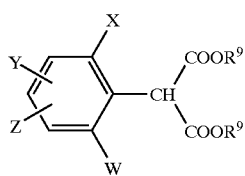

(XXII)

in which

W, X, Y and Z are each as defined above and $R^9$ represents alkyl having 1 to 4 carbon atoms, with alkali metal hydroxides, such as sodium hydroxide or potassium hydroxide, in the presence of a diluent, such as water, at temperatures between 0° C. and 30° C.

In the formula (XXII), W, X, Y and Z each preferably have those meanings which have already been mentioned in connection with the description of the 5,6-dihydro-pyrones of the formula (I) according to the invention as being preferred for these radicals. $R^9$ preferably represents methyl or ethyl.

The substituted phenylmalonic esters of the formula (XXII) are known or can be prepared by known methods (cf. Tetrahedron Letters 27, 2763 (1986) and Organikum, VEB Deutscher Verlag der Wissenschaften, Berlin 1977, p. 587 ff.).

The acyl halides of the formula (VI), carboxylic anhydrides of the formula (VII), chloroformic esters or chloroformic thioesters of the formula (VIII), chloromonothioformic esters or chlorodithioformic esters of the formula (IX), sulphonyl chlorides of the formula (X), phosphorus compounds of the formula (XI) and metal hydroxides, metal alkoxides or amines of the formulae (XII) and (XIII) and isocyanates of the formula (XIV) and carbamoyl chlorides of the formula (XV) furthermore required as starting materials for carrying out the processes (C), (D), (E), (F), (G), (H) and (I) according to the invention are generally known compounds of organic or inorganic chemistry.

The process (A) is characterized in that compounds of the formula (II) in which A, B, $Q^1$, $Q^2$, W, X, Y, Z and $R^8$ are each as defined above are subjected to an intramolecular condensation in the presence of a base.

Suitable diluents for use in the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, iso-propanol, butanol, iso-butanol and tert-butanol.

Suitable bases (deprotonating agents) for carrying out the process (A) according to the invention are all customary proton acceptors. Preference is given to using alkali metals and alkaline earth metal oxides, hydroxides and carbonates, such as sodium hydroxide, potassium hydroxide, magnesium, oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$–$C_{10}$) ammonium chloride) or TDA 1 (=tris-(methoxyethoxyethyl)-amine). It is furthermore possible to use alkali metals such as sodium or potassium. Also suitable are alkali metal and alkaline earth metal amides and hydrides, such as sodium amide, sodium hydride and calcium hydride, and furthermore also alkali metal alkoxides, such as sodium methoxide, sodium ethoxide and potassium tert-butoxide.

When carrying out the process (A) according to the invention, the reaction temperatures can be varied within a relatively wide range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in about double equimolar amounts. However, it is also possible to use a relatively large excess (up to 3 mol) of one component or the other.

Suitable catalysts for carrying out the processes B (α) to B (γ) according to the invention are palladium(0) complexes. Use is made, for example, of tetrakis(tri-phenylphosphine) palladium. Also suitable are palladium(II) compounds, such as bis(triphenylphosphine)palladium(II) chloride.

Suitable acid acceptors for carrying out the processes B (α) and B (γ) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, potassium fluoride or caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process B (γ) according to the invention are water, organic solvents and any mixtures thereof. Examples of organic solvents suitable for processes B (α) to B (γ) are: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl tert-butyl ether, methyl tert-amyl ether, dioxane, tetrahydrofuran, 1,2-dimethoxyethane, 1,2-diethoxyethane, diethylene glycol dimethyl ether or anisole; alcohols, such as methanol, ethanol, n- or iso-propanol, n-, iso-, sec- or tert-butanol, ethanediol, propane-1,2-diol, ethoxyethanol, methoxyethanol, diethylene glycol monomethyl ether; diethylene glycol monoethyl ether; water.

The reaction temperature in process (B) according to the invention can be varied within a relatively wide range. In general, the process is carried out at temperatures between 0° C. and +180° C., preferably between 50° C. and +150° C.

When carrying out the process B (α), silylacetylenes of the formula (III) and compounds of the formulae (I-a') to (I-g') are employed in a molar ratio of from 1:1 to 10:1, preferably from 1:1 to 3:1. When carrying out the process B(β), vinylstannanes of the formula (IV) and compounds of the formulae (I-a') to (I-g') are employed in a molar ratio of from 1:1 to 10:1, preferably from 1:1 to 3:1.

When carrying out the process B (γ) according to the invention, boronic acids of the formula (V) and compounds of the formulae (I-a') and (I-g') are employed in a molar ratio of from 1:1 to 3:1, preferably from 1:1 to 2:1.

The catalyst is generally employed in amounts of from 0.005 to 0.5 mol, preferably from 0.01 to 0.1 mol, per mole of the compounds (I-a') to (I-g'). The base is generally employed in excess.

The process (C-α) is characterized in that compounds of the formula (I-a) are in each case reacted with carbonyl halides of the formula (VI), if appropriate in the presence of a diluent and if appropriate in the presence of an acid binder.

Suitable diluents for use in the process (C-α) according to the invention are all solvents which are inert to the acyl halides. Preference is given to using hydrocarbons, such as benzene, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetra-hydrofuran and dioxane, additionally carboxylic esters, such as ethyl acetate, nitriles, such as acetonitrile, and also strongly polar solvents, such as dimethylformamide, dimethyl sulphoxide and sulpholane. The hydrolytic stability of the acyl halide permitting, the reaction can also be carried out in the presence of water.

Suitable acid binders for the reaction according to the process (C-α) according to the invention are all customary acid acceptors. Preference is given to using tertiary amines, such as triethylamine, pyridine, diazabicyclooctane (DABCO), diazabi-cycloundecene (DBU), diazabicy-clononene (DBN), Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

The reaction temperatures in the process (C-α) according to the invention can be varied within a relatively wide range. In general, the process is carried out at temperatures between −20° C. and +150° C., preferably between 0° C. and 100° C.

When carrying out the process (C-α) according to the invention, the starting materials of the formula (I-a) and the carbonyl halide of the formula (VI) are generally each employed in approximately equivalent amounts. However, it is also possible to use a relatively large excess (up to 5 mol) of carbonyl halide. Work-up is carried out by customary methods.

The process (C-β) is characterized in that compounds of the formula (I-a) are reacted with carboxylic anhydrides of the formula (VII), if appropriate in the presence of a diluent and if appropriate in the presence of an acid binder.

Suitable diluents for use in the process (C-β) according to the invention are preferably those diluents which are also preferred when using acyl halides. Furthermore, it is also possible for excess carboxylic anhydride to act simultaneously as diluent.

Suitable acid binders for process (C-β), which are added, if appropriate, are preferably those acid binders which are also preferred when using acyl halides.

The reaction temperatures in the process (C-β) according to the invention can be varied within a relatively wide range. In general, the process is carried out at temperatures between −20° C. and +150° C., preferably between 0° C. and 100° C.

When carrying out the process (C-β) according to the invention, the starting materials of the formula (I-a) and the carboxylic anhydride of the formula (VII) are generally each employed in approximately equivalent amounts. However, it is also possible to use a relatively large excess (up to 5 mol) of carboxylic anhydride. Work-up is carried out by customary methods.

In general, diluent and excess carboxylic anhydride and the carboxylic acid formed are removed by distillation or by washing with an organic solvent or with water.

The process (D) is characterized in that compounds of the formula (I-a) are in each case reacted with chloroformic esters or chloroformic thioesters of the formula (VIII), if appropriate in the presence of a diluent and if appropriate in the presence of an acid binder.

Acid binders suitable for the reaction according to process (D) according to the invention are all customary acid acceptors. Preference is given to using tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for use in the process (D) according to the invention are all solvents which are inert to the chloroformic esters or chloroformic thioesters. Preference is given to using hydrocarbons, such as benzene, benzene, toluene, xylene and tetralin, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, nitriles, such as acetonitrile, and also strongly polar solvents, such as dimethylformamide, dimethyl sulphoxide and sulpholane.

When carrying out the process (D) according to the invention, the reaction temperatures can be varied within a relatively wide range. If the reaction is carried out in the presence of a diluent and an acid binder, the reaction temperatures are generally between −20° C. and +100° C., preferably between 0° C. and 50° C.

The process (D) according to the invention is generally carried out under atmospheric pressure.

When carrying out the process (D) according to the invention, the starting materials of the formula (I-a) and the appropriate chloroformic ester or chloroformic thioester of the formula (VIII) are generally each employed in approximately equivalent amounts. However, it is also possible to use a relatively large excess (up to 2 mol) of one component or the other. Work-up is carried out by customary methods. In general, precipitated salts are removed, and the reaction mixture that remains is concentrated by removing the diluent under reduced pressure.

The process (E) according to the invention is characterized in that compounds of the formula (I-a) are in each case reacted with compounds of the formula (IX) in the presence of a diluent and, if appropriate, in the presence of an acid binder.

In preparation process (E), about 1 mol of chloromonothioformic ester or chlorodithioformic ester of the formula (IX) are employed per mole of starting material of the formula (I-a), at from 0 to 120° C., preferably from 20 to 60° C.

Suitable diluents, which are added, if appropriate, are all inert polar organic solvents, such as nitriles, ethers, esters, amides, sulphones, sulphoxides, but also halogenoalkanes.

Preference is giving to using acetonitrile, ethyl acetate, dimethyl sulphoxide, tetrahydrofuran, dimethylformamide or methylene chloride.

If, in a preferred embodiment, the enolate salt of the compound (I-a) is prepared by addition of strong deprotonating agents, such as, for example, sodium hydride or potassium tert-butoxide, the further addition of acid binders can be dispensed with.

If acid binders are used, these can be customary inorganic or organic bases, examples that may be mentioned being sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (F) according to the invention is characterized in that compounds of the formula (I-a) are in each case reacted with sulphonyl chlorides of the formula (X), if appropriate in the presence of a diluent and if appropriate in the presence of an acid binder.

In preparation process (F), about 1 mol of sulphonyl chloride of the formula (X) is used per mole of starting material of the formula, at from −20 to 150° C., preferably from 20 to 70° C.

Suitable diluents, which are added, if appropriate, are all inert polar organic solvents, such as esters, ethers, amides, nitrites, sulphones, sulphoxides, or halogenated hydrocarbons, such as methylene chloride.

Preference is given to using acetonitrile, ethyl acetate, dimethyl sulphoxide, tetrahydrofuran, dimethylformamide of methylene chloride.

If, in a preferred embodiment, the enolate salt of the compound (I-a) is prepared by addition of strong deprotonating agents (such as, for example, sodium hydride or potassium tert-butoxide), the further addition of acid binders can be dispensed with.

If acid binders are used, these can be customary inorganic or organic bases, examples which may be mentioned being sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods.

The process (G) according to the invention is characterized in that compounds of the formula (I-a) are in each case reacted with phosphorus compounds of the formula (XI), if appropriate in the presence of a diluent and if appropriate in the presence of an acid binder.

In preparation process (G), from 1 to 2, preferably from 1 to 1.3, mol of the phosphorus compound of the formula (XI) are used per mole of the compound (I-a), at temperatures between −40° C. and 150° C., preferably between −10 and 110° C., to give compounds of the formula (I-e).

Suitable diluents which may be added, if appropriate, are all inert polar organic solvents, such as ethers, amides, nitriles, alcohols, sulphides, sulphones, sulphoxides. etc.

Preference is given of using acetonitrile, dimethyl sulphoxide, tetrahydrofuran, dimethylformamide or methylene chloride.

Suitable acid binders, which may be added, if appropriate, are customary inorganic or organic bases, such as hydroxides, carbonates or amines. Examples which may be mentioned are sodium hydroxide, sodium carbonate, potassium carbonate, pyridine and triethylamine.

The reaction can be carried out at atmospheric pressure or under elevated pressure and is preferably carried out at atmospheric pressure. Work-up is carried out by customary methods of organic chemistry. The purification of the resulting end product is preferably carried out by crystallization, chromatographic purification or by so-called "incipient distillation", i.e. removal of the volatile components under reduced pressure.

The process (H) is characterized in that compounds of the formula (I-a) are reacted with metal hydroxides or metal alkoxides of the formula (XII) or amines of the formula (XIII), if appropriate in the presence of a diluent.

Preferred diluents for the process (H) according to the invention are ethers, such as tetrahydrofuran, dioxane or diethyl ether, or else alcohols, such as methanol, ethanol, isopropanol, but also water.

The process (H) according to the invention is generally carried out under atmospheric pressure.

The reaction temperatures are generally between −20° C. and 100° C., preferably between 0° C. and 50° C.

The process (I) according to the invention is characterized in that (I-α) compounds of the formula (I-a) are in each case reacted with compounds of the formula (XIV), if appropriate in the presence of a diluent and if appropriate in the presence of a catalyst, or (I-β) with compounds of the formula (XV), if appropriate in the presence of a diluent and if appropriate in the presence of an acid binder.

In preparation process (I-α), about 1 mol of isocyanate of the formula (XIV) is used per mole of starting material of the formula (I-a), at from 0 to 100° C., preferably at from 20 to 50° C.

Suitable diluents which are added, if appropriate, are all inert organic solvents, such as nitrites, esters, ethers, amides, sulphones and sulphoxides.

If appropriate, catalysts may be added to accelerate the reaction. Particularly advantageous catalysts are organotin compounds, such as, for example, dibutyltin dilaurate. The process is preferably carried out at atmospheric pressure.

In preparation process (I-β), about 1 mol of carbamoyl chloride of the formula (XV) is used per mole of starting material of the formula (I-a), at from −20 to 150° C., preferably at from 0 to 70° C.

Suitable diluents which are added, if appropriate, are all inert polar organic solvents, such as nitrites, esters, ethers, amides, sulphones, sulphoxides, or halogenated hydrocarbons.

Preference is given to using acetonitrile, ethyl acetate, dimethyl sulphoxide, tetrahydrofuran, dimethylformamide or methylene chloride.

If, in a preferred embodiment, the enolate salt of the compound (I-a) is prepared by addition of strong deprotonating agents (such as, for example, sodium hydride or potassium tert-butoxide), the further addition of acid binders can be dispensed with.

If acid binders are used, these can be customary inorganic or organic bases, examples which may be mentioned being sodium hydroxide, sodium carbonate, potassium carbonate, triethylamine and pyridine.

The reaction can be carried out at atmospheric pressure or under elevated pressure and is preferably carried out at atmospheric pressure. Work-up is carried out by customary methods.

Suitable diluents for carrying out the process (J) according to the invention are all customary organic solvents which are inert towards the reactants. Preference is given to using hydrocarbons, such as o-dichlorobenzene, tetralin, toluene and xylene, furthermore ethers, such as dibutyl ether, glycol dimethyl ether and diglycol dimethyl ether, moreover polar solvents, such as dimethyl sulphoxide, sulpholane, dimethylformamide or N-methylpyrrolidone. Suitable cosolvents according to Example (I-2-a) are alcohols, such as methanol, ethanol, propanol or butanol, but also water.

Suitable acid acceptors for carrying out the process (J) according to the invention are all customary acid binders.

Preference is giving to using tertiary amines, such as triethylamine, pyridine, diazabicyclooctane (DABCO), diazabicycloundecene (DBU), diazabicyclononene (DBN), Hünig base or N,N-dimethylaniline.

When carrying out the process (J) according to the invention, the reaction temperatures can be varied within a relatively wide range. The process is expediently carried out at temperatures between 0° C. and 250° C., preferably between 50° C. and 220° C.

The process (J) according to the invention is preferably carried out under atmospheric pressure.

When carrying out the process (J) according to the invention, in general an equimolar amount of the ketene derivative of the formula (XVII) and if appropriate also an equimolar amount of acid acceptor are used per mole of silyl ether of the formula (XVI). However, it is also possible to use a relatively large excess (up to 5 mol) of one component or the other.

The 5,6-dihydro-pyrones of the formula (I) according to the invention have very good pesticidal activity and are highly compatible with crop plants.

The active compounds are suitable for controlling animal pests, in particular insects, arachnids and nematodes found in agriculture, in forests, in the protection of stored products and materials and in the hygiene sector, and they are tolerated well by plants and have favourable homeotherm toxicity. They are preferably employed as crop protection agents. They are active against normally sensitive and resistant species, and against all or individual developmental stages. The abovementioned pests include:

From the order of the *Isopoda*, for example, *Oniscus asellus, Armadillidium vulgare, Porcellio scaber.*

From the order of the *Diplopoda*, for example, *Blaniulus guttulatus.*

From the order of the *Chilopoda*, for example, *Geophilus carpophagus, Scutigera* spp.

From the order of the *Symphyla*, for example, *Scutigerella immaculata.*

From the order of the *Thysanura*, for example, *Lepisma saccharina.*

From the order of the *Collembola*, for example, *Onychiurus armatus.*

From the order of the *Orthoptera*, for example, *Acheta domesticus, Gryllotalpa* spp., *Locusta migratoria migratorioides, Melanoplus* spp., *Schistocerca gregaria.*

From the order of the *Blattaria*, for example, *Blatta orientalis, Periplaneta americana, Leucophaea maderae, Blattella germanica.*

From the order of the *Dermaptera*, for example, *Forficula auricularia.*

From the order of the *Isoptera*, for example, *Reticulitermes* spp.

From the order of the *Phthiraptera*, for example, *Pediculus humanus corporis, Haematopinus* spp., *Linognathus* spp., *Trichodectes* spp., *Damalinia* spp.

From the order of the *Thysanoptera*, for example, *Hercinothrips femoralis, Thrips tabaci, Thrips palmi, Frankliniella occidentalis.*

From the order of the *Heteroptera*, for example, *Eurygaster* spp., *Dysdercus intermedius, Piesma quadrata, Cimex lectularius, Rhodnius prolixus, Triatoma* spp.

From the order of the *Homoptera*, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the *Lepidoptera*, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the *Coleoptera*, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the *Hymenoptera*, for example, *Diprion* spp., *Hoplocampa* spp., *Lasius* spp., *Monomorium pharaonis, Vespa* spp.

From the order of the *Diptera*, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the *Siphonaptera*, for example, *Xenopsylla cheopis, Ceratophyllus* spp.

From the class of the *Arachnida*, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

At certain concentrations or application rates, the compounds according to the invention can, if appropriate, also be employed as herbicides and microbicides, for example as fungicides, antimycotics and bactericides. If appropriate, they can also be used as intermediates or precursors for the synthesis of further active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixing components are the following:

Fungicides aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoro-methyl-1,3-thiazole-5-carboxanilide,
2,2-dichloro-N-[1-(4-chlorophenyl)-ethyl]-1-ethyl-3-methyl-cyclopropane-carboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole.
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propinyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine-hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
4-[3,4-dimethoxyphenyl-3-(4-fluorophenyl)-acryloxy]-morpholine.

Bactericides
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides
abamectin, acephate, acetamiprid, acrinathrin, alanycarb, aldicarb, aldoxycarb, alpha-cypernethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluorone, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cyclopene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, lambda-cyhalothrin, lufenuron, malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, rilbemycin, monocrotophos, naled, nitenpyram, nithiazine, novaluron, nuclear polyhedrosis viruses, omethoat, oxamyl, oxydemethon M,

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, thetacypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos (1R-cis)-[5-(phenylmethyl)-3-furanyl]-methyl-3-[(dihydro-2-oxo-3(2H)-furanylidene)-methyl]-2,2-dimethylcyclopropane carboxylate (3-phenoxyphenyl)-methyl-2,2,3,3-tetramethylcyclopropane carboxylate 1-[(2-chloro-5-thiazolyl)methyl]tetrahydro-3,5-dimethyl-N-nitro-1,3,5-triazine-2(1H)-imine 2-(2-chloro-6-fluorophenyl)-4-[4-(1,1-dimethylethyl)phenyl]-4,5-dihydro-oxazole 2-(acetlyoxy)-3-dodecyl-1,4-naphthalenedione 2-chloro-N-[[[4-(1-phenylethoxy)-phenyl]-amino]-carbonyl]-benzamide 2-chloro-N-[[[4-(2,2-dichloro-1,1-difluoroethoxy)-phenyl]-amino]-carbonyl]-benzamide 3-methylphenyl propylcarbamate 4-[4-(4-ethoxyphenyl)-4-methylpentyl]-1-fluoro-2-phenoxy-benzene 4-chloro-2-(1,1-dimethylethyl)-5-[[2-(2,6-dimethyl-4-phenoxyphenoxy)ethyl]thio]-3(2H)-pyridazinone 4-chloro-2-(2-chloro-2-methylpropyl)-5-[(6-iodo-3-pyridinyl)methoxy]-3(2H)-pyridazinone 4-chloro-5-[(6-chloro-3-pyridinyl)methoxy]-2-(3,4-dichlorophenyl)-3(2H)-pyridazinone

*Bacillus thuringiensis* strain EG-2348

[2-benzoyl-1-(1,1-dimethylethyl)-hydrazinobenzoic acid 2,2-dimethyl-3-(2,4-dichlorophenyl)-2-oxo-1-oxaspiro[4.5] dec-3-en-4-yl butanoate

[3-[(6-chloro-3-pyridinyl)methyl]-2-thiazolidinylidene]-cyanamide dihydro-2-(nitromethylene)-2H-1,3-thiazine-3(4H)-carboxaldehyde ethyl [2-[[1,6-dihydro-6-oxo-1-(phenylmethyl)-4-pyridazinyl]oxy]ethyl]-carbamate N-(3,4,4-trifluoro-1-oxo-3-butenyl)-glycine N-(4-chlorophenyl)-3-[4-(difluoromethoxy)phenyl]-4,5-dihydro-4-phenyl-1H-pyrazole-1-carboxamide N-[(2-chloro-5-thiazolyl)methyl]-N'-methyl-N''-nitro-guanidine N-methyl-N'-(1-methyl-2-propenyl)-1,2-hydrazinedicarbothioamide N-methyl-N'-2-propenyl-1,2-hydrazinedicarbothioamide O,O-diethyl [2-(dipropylamino)-2-oxoethyl]-ethylphosphoramidothioate.

N-cyanomethyl-4-trifluoromethyl-nicotinamide 3,5-dichloro-1-(3,3-dichloro-2-propenyloxy)-4-[3-(5-trifluoromethyl-pyridin-2-yloxy)-propoxy]-benzene.

Mixtures with other known active compounds such as herbicides or with fertilizers and growth regulators are also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms. When used against hygiene pests and stored-product pests, the active compound is distinguished by an excellent residual action on wood and clay as well as good stability to alkali on limed substrates.

The active compounds according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, hair lice, bird lice and fleas. These parasites include:

From the order of the *Anoplurida*, for example, *Haematopinus* spp., *Linognathus* spp., *Pediculus* spp., *Phtirus* spp., *Solenopotes* spp.

From the order of the *Mallophagida* and the suborders *Amblycerina* and *Ischnocerina*, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order *Diptera* and the suborders *Nematocerina* and *Brachycerina*, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the *Siphonapterida*, for example, *Pulex* spp., *Ctenocephalides* spp., *Xenopsylla* spp., *Ceratophyllus* spp.

From the order of the *Heteropterida*, for example, *Cimex* spp., *Triatoma* spp., *Rhodnius* spp., *Panstmongylus* spp.

From the order of the *Blattarida*, for example, *Blatta orientalis, Periplaneta americana, Blattela germanica, Supella* spp.

From the subclass of the *Acaria* (*Acarida*) and the orders of the *Meta-* and *Mesostigmata*, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the *Actinedida* (*Prostigmata*) and *Acaridida* (*Astigmata*), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compounds according to the invention.

The active compounds according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compounds can be applied as formulations (for example powders, emulsions, flowables) comprising the active compounds in an amount of 1 to 80% by weight, either directly or after 100- to 10 000-fold dilution, or they may be used as a chemical dip.

Moreover, it has been found that the active compounds according to the invention show a potent insecticidal action against insects which destroy industrial materials.

The following insects may be mentioned by way of example and with preference, but not by way of limitation:

Beetles such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis. Reticulitermes lucifugus, Mastotermes darwiniensis, Zootermopsis nevadensis, Coptotermes formosanus.*

Bristle-tails such as *Lepisma saccharina.*

Industrial materials in the present context are understood as meaning non-living materials such as, preferably, polymers, adhesives, glues, paper and board, leather, wood, timber products and paints.

The materials which are to be protected from insect attack is very especially preferably wood and timber products.

Wood and timber products which can be protected by the composition according to the invention, or mixtures comprising it, are to be understood as meaning, for example: construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compounds can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of terpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the insecticide-fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The ready-to-use compositions can also comprise other insecticides, if appropriate, and also one or more fungicides, if appropriate.

Possible additional mixing components are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The combinations according to the invention can at the same time be employed for protecting objects which come into contact with saltwater or brackish water, such as hulls, screens, nets, buildings, moorings and signalling systems, against fouling.

Fouling by sessile *Oligochaeta*, such as *Serpulidae*, and by shells and species from the *Ledamorpha* group (goose barnacles), such as various *Lepas* and *Scalpellum* species, or by species from the *Balanomorpha* group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile *Entomostraka* groups, which come under the generic term *Cirripedia* (cirriped crustaceans), is of particular importance.

Surprisingly, it has now been found that the compounds according to the invention, alone or in combination with other active compounds, have an outstanding antifouling action.

Using the combinations according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as
fentin acetate, metaldehyde, methiocarb, niclosamid, thiodicarb and trimethacarb;

or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleiimide.

The antifouling compositions used comprise the active compound according to the invention of the compositions according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and excipients in domestic insecticide products for controlling these pests. They are active against sensitive and resistant species and against all developmental stages. These pests include:

From the order of the *Scorpionidea*, for example, *Buthus occitanus*.

From the order of the *Acarina*, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neu-trombicula autumnalis, Dermatophagoides pteronissimus, Dermatophagoides forinae*.

From the order of the *Araneae*, for example, *Aviculariidae, Araneidae*.

From the order of the *Opiliones*, for example, *Pseudoscorpiones chelifer, Pseudoscorpiones cheiridium, Opiliones phalangium*.

From the order of the *Isopoda*, for example, *Oniscus asellus, Porcellio scaber*.

From the order of the *Diplopoda*, for example, *Blaniulus guttulatus, Polydesmus* spp.

From the order of the *Chilopoda*, for example, *Geophilus* spp.

From the order of the *Zygentoma*, for example, *Ctenolepisma* spp., *Lepisma saccharina, Lepismodes inquilinus*.

From the order of the *Blattaria*, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the *Saltatoria*, for example, *Acheta domesticus*.

From the order of the *Dermaptera*, for example, *Forficula auricularia*.

From the order of the *Isoptera*, for example, *Kalotermes* spp., *Reticulitermes* spp.

From the order of the *Psocoptera*, for example, *Lepinatus* spp., *Liposcelis* spp.

From the order of the *Coleptera*, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the *Diptera*, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the *Lepidoptera*, for example, *Achroia grisella, Galleria mellonella, Plodia interpunctella, Tinea cloacella, Tinea pellionella, Tineola bisselliella*.

From the order of the *Siphonaptera*, for example, *Ctenocephalides canis, Ctenoccphalides felis, Pulex irritans, Tunga penetrans, Xenopsylla cheopis*.

From the order of the *Hymenoptera*, for example, *Camponlotus herculcanus, Lasius fuliginosus, Lasius niger, Lasius umbratus, Monomorium pharaonis, Paravespula* spp., *Tetramorium caespitum*.

From the order of the *Anoplura*, for example, *Pediculus humanus capitis, Pediculus humanus corporis, Phthirus pubis*.

From the order of the *Heteroptera*, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutiloin, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

As already mentioned above, it is possible to treat all plants and their parts according to the invention. In a preferred embodiment, wild plant species and cultivars, or those obtained by conventional biological breeding, such as crossing or protoplast fusion, and parts thereof, are treated. In a further preferred embodiment, transgenic plants and cultivars obtained by genetical engineering, if appropriate in combination with conventional methods (Genetically Modified Organisms), and parts thereof are treated. The term "parts" or "parts of plants" or "plant parts" has been explained above.

Particularly preferably, plants of the cultivars which are in each case commercially available or in use are treated according to the invention. Cultivars are to be understood as meaning plants having certain properties ("traits") and which have been obtained by conventional breeding, by mutagenesis or by recombinant DNA techniques. They can be varieties, bio- or genotypes.

Depending on the plant species or cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or cultivars (i.e. those obtained by genetical engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to cultivars having these genetic traits or genetic traits still to be developed, which plants will be developed and/or marketed in the future.

The plants listed can be treated according to the invention in a particularly advantageous manner with the compounds of the formula (I). The preferred ranges stated above for the active compounds also apply to the treatment of these plants. Particular emphasis is given to the treatment of plants with the mixtures specifically mentioned in the present text.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnhaplhthalenies, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95%. by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, BAS-662H, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chloitoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, naproparide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop(-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example I-a-1

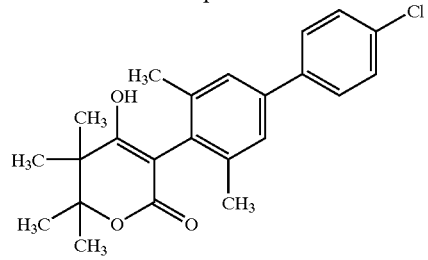

5.6 g (50 mmol) of potassium tert-butoxide are initially charged in 30 ml of absolute DMF and, at 60° C., admixed with 10.6 g of the compound according to Example II-8 in 20 ml of DMF. The reaction solution is stirred at 60° C. for 3 hours, poured into ice-water and acidified with concentrated hydrochloric acid. The precipitate is filtered off with suction, washed and dried.

Yield: 7.4 g (77% of theory), m.p. >220° C.

Example I-a-2

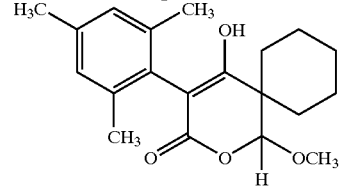

9.8 g (44 mmol) of 2,4,5-trimethylphenyl chlorocarbonyl ketene are initially charged in 80 ml of anhydrous xylene and, at 20° C., 8.1 g (44 mmol) of trimethylsityloxymethylidenecyclohexane in 30 ml of anhydrous xylene are added dropwise with exclusion of moisture. The mixture is heated at reflux for 8 hours, 7.3 ml of methanol are then added, and heating at reflux is continued for another 2 hours. The mixture is washed with water and saturated sodium chloride solution and dried over sodium sulphate. The mixture is concentrated under reduced pressure and the residue is chromatographed on silica gel (35 to 70 μm) using toluene/acetone (20:1).

Yield: 3.9 g (≙27% of theory). m.p. 174–175° C.

Example I-a-3

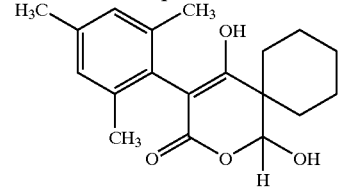

9.4 g (42.2 mmol) of 2,4,5-trimethylphenyl chlorocarbonyl ketene are initially charged in 80 ml of anhydrous xylene and, at 20° C., 7.1 g (42.2 mmol) of trimethylsilyloxymethylidenecyclopentane in 30 ml of anhydrous xylene are added dropwise with exclusion of moisture. The mixture is heated at reflux for 8 hours and then washed with water and saturated sodium chloride solution, and the organic phase is dried over sodium sulphate. The organic phase is evaporated and the residue is chromatographed on silica gel (35 to 70 μm) using the mobile phase toluene.

Yield: 3.2 g (≙25% of theory). m.p. 122–124° C.

The following compounds of the formula I-a are obtained analogously to Examples I-a-1, I-a-2 and I-a-3 and in accordance with the general statements on the preparation

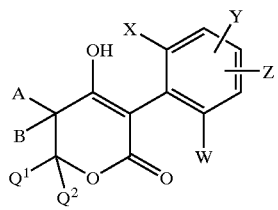
(I-a)

| Ex. No. | W | X | Y | Z | B | A | Q¹ | Q² | m.p. ° C. |
|---|---|---|---|---|---|---|---|---|---|
| I-a-4 | H | $CH_3$ | 4-Cl | H | $CH_3$ | $CH_3$ | $OCH_3$ | H | 164–166 |
| I-a-5 | H | $CH_3$ | 5-(4-Cl—$C_6H_4$) | H | $CH_3$ | $CH_3$ | H | H | wax |
| I-a-6 | H | $CH_3$ | 5-(4-Cl—$C_6H_4$) | H | $CH_3$ | $CH_3$ | $CH_3$ | $CH_3$ | 125 |
| I-a-7 | $CH_3$ | $CH_3$ | 4-$CH_3$ | H | $CH_3$ | $CH_3$ | $CH_3$ | $CH_3$ | 140 |
| I-a-8 | H | $CH_3$ | 5-$CH_3$ | H | $CH_3$ | $CH_3$ | $OCH_3$ | H | oil |
| I-a-9 | $CH_3$ | $CH_3$ | 3-$CH_3$ | 4-$CH_3$ | $CH_3$ | $CH_3$ | $OCH_3$ | H | 121–122 |
| I-a-10 | $CH_3$ | $CH_3$ | 3-$CH_3$ | 4-$CH_3$ | $CH_3$ | $CH_3$ | OH | H | 184–186 |
| I-a-11 | $CH_3$ | $CH_3$ | 4-$CH_3$ | H | $CH_3$ | $CH_3$ | $OCH_3$ | H | 115–117 |
| I-a-12 | $CH_3$ | $CH_3$ | 4-$CH_3$ | H | \multicolumn{3}{c}{$CH_2$—$CCH_3$—$(CH_2)_2$} | H | 171 |
| I-a-13 | $CH_3$ | $CH_3$ | 4-(4-Cl—$C_6H_4$) | H | $CH_3$ | $CH_3$ | H | H | 174 |
| I-a-14 | $CH_3$ | $CH_3$ | 4-$CH_3$ | H | $CH_3$ | $CH_3$ | $OC_2H_5$ | H | 90–93 |
| I-a-15 | $CH_3$ | $CH_3$ | 4-$CH_3$ | H | —$(CH_2)_5$— | | $OC_2H_5$ | H | 148–150 |
| I-a-16 | $CH_3$ | $CH_3$ | 4-$CH_3$ | H | $CH_3$ | $CH_3$ | $OC_3H_7$ | H | 108–110 |
| I-a-17 | $CH_3$ | $CH_3$ | 4-$CH_3$ | H | $CH_3$ | $C_2H_5$ | $OCH_3$ | H | 111–113 |
| I-a-18 | $CH_3$ | $CH_3$ | 4-$CH_3$ | H | $C_2H_5$ | $C_2H_5$ | $OCH_3$ | H | 123–125 |
| I-a-19 | $CH_3$ | $CH_3$ | 4-$CH_3$ | H | —$(CH_2)_5$— | | OH | H | 154–156 |
| I-a-20 | H | $CH_3$ | 5-(3-Cl—$C_6H_4$) | H | $CH_3$ | $CH_3$ | $CH_3$ | $CH_3$ | oil |
| I-a-21 | H | $CH_3$ | 5-(4-Cl—$C_6H_4$) | 4-$CH_3$ | $CH_3$ | $CH_3$ | $CH_3$ | $CH_3$ | 182–184° C. |
| I-a-22 | $CH_3$ | $CH_3$ | 5-(4-Cl—$C_6H_4$) | 4-$CH_3$ | $CH_3$ | $CH_3$ | $CH_3$ | $CH_3$ | 233–234° C. |
| I-a-23 | H | $CH_3$ | 5-Br | H | $CH_3$ | $CH_3$ | $CH_3$ | $CH_3$ | 184–186° C. |
| I-a-24 | H | $CH_3$ | 5-(3,5-$Cl_2$—$C_6H_3$) | H | $CH_3$ | $CH_3$ | $CH_3$ | $CH_3$ | 192–193° C. |
| I-a-25 | H | $CH_3$ | 5-(2-$CH_3$, 4-Cl—$C_6H_3$) | H | $CH_3$ | $CH_3$ | $CH_3$ | $CH_3$ | 202–203° C. |
| I-a-26 | H | $CF_3$ | 4-Cl | H | $CH_3$ | $CH_3$ | $CH_3$ | $CH_3$ | 185–186° C. |
| I-a-27 | Br | $C_3H_7$ | 4-Br | H | $CH_3$ | $CH_3$ | $CH_3$ | $CH_3$ | oil |
| I-a-28 | $C_2H_5$ | $C_2H_5$ | 4-Br | H | $CH_3$ | $CH_3$ | $CH_3$ | $CH_3$ | 178–180° C. |
| I-a-29 | Cl | Cl | 4-$CF_3$ | H | $CH_3$ | $CH_3$ | $CH_3$ | $CH_3$ | 233–234° C. |
| I-a-30 | Cl | Cl | 4-Cl | H | $CH_3$ | $CH_3$ | $CH_3$ | $CH_3$ | >250° C. |
| I-a-31 | H | Cl | 5-(4-Cl—$C_6H_4$) | H | $CH_3$ | $CH_3$ | $CH_3$ | $CH_3$ | 204–205° C. |

Example I-A-b-1

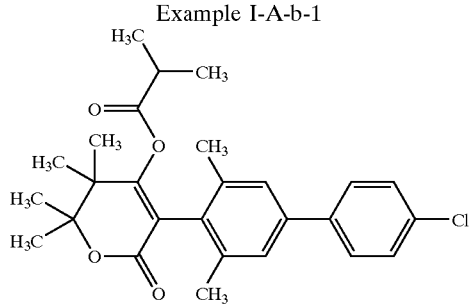

1.5 g (3.9 mmol) of the compound according to Example I-a-1 are initially charged in 15 ml of anhydrous dichloromethane and admixed with 0.78 ml (5.85 mmol) of triethylamine. At 0° C., 0.57 g (5.07 mmol) of isobutyryl chloride are added, and the mixture is stilled at room temperature for 2 hours. The reaction solution is extracted with 10% strength citric acid and washed with dichloromethane. The mixture is then extracted with 1 N NaOH and washed once more with dichloromethane and dried, and the solvent is evaporated.

Yield: 1.2 g ($\triangleq$68% of theory).

$^1$H-NMR (400 MHz, DMSO): δ=0.69 (d, 6H, (CH$_3$)$_2$—CH); 1.17 (s, 6H, (CH$_3$)$_2$—C), 1.52 (s, 6H, (CH$_3$)$_2$—C—O), 2.11 (s, 6H, 2 Ar—CH$_3$) ppm.

The following compounds of the formulae (I-A-b) and (I-B-b) are obtained analogously to Examples (I-A-b-1) and in accordance with the general statements on the preparation

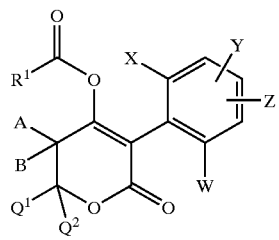

(I-A-b)

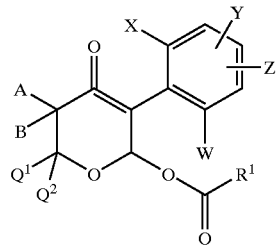

(I-B-b)

| Ex. No. | W | X | Y | Z | B | A | Q$^1$ | Q$^2$ | R$^1$ | m.p. ° C. |
|---|---|---|---|---|---|---|---|---|---|---|
| I-A-b-2 | H | CH$_3$ | 5-CH$_3$ | H | CH$_3$ | CH$_3$ | OCH$_3$ | H | CH$_3$ | oil |
| I-A-b-3 | H | CH$_3$ | 4-Cl | H | CH$_3$ | CH$_3$ | OCH$_3$ | H | CH$_3$ | oil |
| I-A-b-4 | CH$_3$ | CH$_3$ | 4-CH$_3$ | H | CH$_2$—CCH$_3$—(CH$_2$)$_2$ | | | H | CH(CH$_3$)$_2$ | 84–86 |
| I-A-b-5 | CH$_3$ | CH$_3$ | 4-CH$_3$ | H | CH$_3$ | CH$_3$ | OCH$_3$ | H | CH$_3$ | 118–120 |
| I-A-b-6 | CH$_3$ | CH$_3$ | 4-CH$_3$ | H | CH$_3$ | CH$_3$ | OCH$_3$ | H | 2-Cl-pyridin-5-yl | 115–117 |
| I-A-b-7 | CH$_3$ | CH$_3$ | 4-CH$_3$ | H | CH$_3$ | CH$_3$ | OCH$_3$ | H | 4-Cl-phenyl | oil |
| I-A-b-8 | CH$_3$ | CH$_3$ | 4-CH$_3$ | H | CH$_3$ | CH$_3$ | O—COCH$_3$ | H | CH$_3$ | 125–127 |
| I-A-b-9 | CH$_3$ | CH$_3$ | 4-CH$_3$ | H | —(CH$_2$)$_4$— | | O—COCH$_3$ | H | CH$_3$ | 122–124 |

-continued (I-A-b)

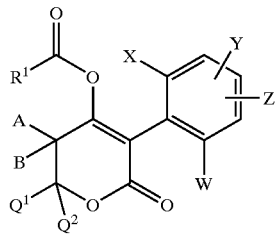

(I-B-b)

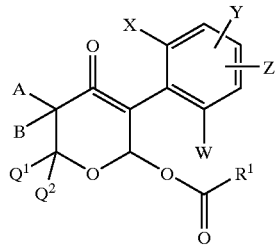

| Ex. No. | W | X | Y | Z | B | A | Q$^1$ | Q$^2$ | R$^1$ | m.p. ° C. |
|---|---|---|---|---|---|---|---|---|---|---|
| I-A-b-10 | H | CH$_3$ | 5-(4-Cl—C$_6$H$_4$) | H | CH$_3$ | CH$_3$ | CH$_3$ | CH$_3$ | i-C$_3$H$_7$ | oil |
| I-A-b-11 | CH$_3$ | CH$_3$ | 4-(4-Cl—C$_6$H$_4$) | H | CH$_3$ | CH$_3$ | H | H | i-C$_3$H$_7$ | oil |
| I-B-b-12 | H | CH$_3$ | 5-CH$_3$ | H | CH$_3$ | CH$_3$ | OCH$_3$ | H | CH$_3$ | oil |
| I-B-b-13 | H | CH$_3$ | 4-Cl | H | CH$_3$ | CH$_3$ | OCH$_3$ | H | CH$_3$ | oil |
| I-B-b-14 | CH$_3$ | CH$_3$ | 4-CH$_3$ | H | CH$_3$ | CH$_3$ | OCH$_3$ | H | CH$_3$ | 110–113 |
| I-B-b-15 | CH$_3$ | CH$_3$ | 4-CH$_3$ | H | CH$_3$ | CH$_3$ | OCH$_3$ | H |  | 134–136 |
| I-B-b-16 | CH$_3$ | CH$_3$ | 4-CH$_3$ | H | CH$_3$ | CH$_3$ | CH$_3$ | CH$_3$ | i-C$_3$H$_7$ | oil |
| I-B-b-17 | CH$_3$ | CH$_3$ | 4-CH$_3$ | H | CH$_3$ | CH$_3$ | H | H | i-C$_3$H$_7$ | 88–91 |
| I-A-b-18 | H | CH$_3$ | 5-(4-Cl—C$_6$H$_4$) | H | CH$_3$ | CH$_3$ | H | H | i-C$_3$H$_7$ | oil |

Isomer mixtures of the formulae I-A-b and I-B-b were separated by silica gel column chromatography.

Example I-A-c-1

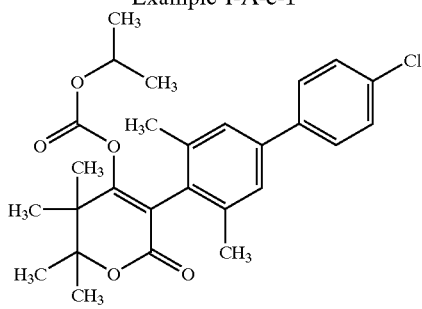

1.5 g (3.9 mmol) of the compound according to Example I-a-1 are initially charged in 15 ml of anhydrous dichloromethane and admixed with 0.78 ml (5.85 mmol) of triethylamine. At 0° C., 0.63 g (5.07 mmol) of isopropyl chloroformate are added, and the mixture is stirred at room temperature for 2 hours. The reaction solution is extracted with 10% strength citric acid and washed with dichloromethane. The mixture is then extracted with 1 N NaOH and washed once more with dichloromethane and dried, and the solvent is evaporated.

Yield: 1.2 g (≙65% of theory).

$^1$H-NMR (400 MHz, DMSO): δ=1.08 (d, 6H, (CH$_3$)$_2$—CH); 1.16 (s, 6H, (CH$_3$)$_2$—C), 2.11 (s, 6H, 2 Ar—CH$_3$), 7.36 (s, 2H, 2 Ar—H) ppm.

The following compounds of the formulae (I-A-c) and (I-B-c) were obtained analogously to Example I-A-c-1 and in accordance with the general statements on the preparation (I-A-c)

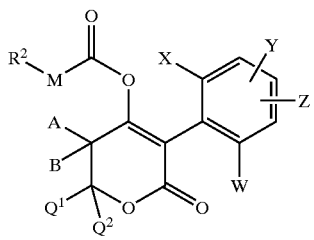

(I-B-c)

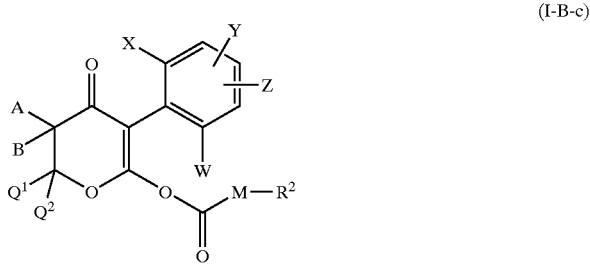

| Ex. No. | W | X | Y | Z | B | A | Q¹ | Q² | M | R² | m.p. °C. |
|---|---|---|---|---|---|---|---|---|---|---|---|
| I-A-c-2 | $CH_3$ | $CH_3$ | 4-$CH_3$ | H | $CH_3$ | $CH_3$ | $OCH_3$ | H | O | $CH_3$ | 108–110 |
| I-A-c-3 | H | $CH_3$ | 5-(4-Cl—$C_6H_4$) | H | $CH_3$ | $CH_3$ | $CH_3$ | $CH_3$ | O | i-$C_3H_7$ | oil |
| I-A-c-4 | $CH_3$ | $CH_3$ | 4-(4-Cl—$C_6H_4$) | H | $CH_3$ | $CH_3$ | H | H | O | i-$C_3H_7$ | oil |
| I-B-c-1 | $CH_3$ | $CH_3$ | 4-$CH_3$ | H | $CH_3$ | $CH_3$ | H | H | O | i-$C_3H_7$ | oil |
| I-B-c-2 | $CH_3$ | $CH_3$ | 4-$CH_3$ | H | $CH_2$—$CCH_3$—$(CH_2)_2$ | | | H | O | i-$C_3H_7$ | oil |
| I-B-c-7 | $CH_3$ | $CH_3$ | 4-$CH_3$ | H | $CH_3$ | $CH_3$ | H | H | O | i-$C_3H_7$ | oil |
| I-A-c-8 | H | $CH_3$ | 5-(4-Cl—$C_6H_4$) | H | $CH_3$ | $CH_3$ | H | H | O | $C_2H_5$ | oil |
| I-A-c-9 | H | $CH_3$ | 5-(4-Cl—$C_6H_4$) | H | $CH_3$ | $CH_3$ | $CH_3$ | $CH_3$ | O | $C_2H_5$ | 144 |
| I-A-c-10 | H | $CH_3$ | 5-(4-Cl—$C_6H_4$) | 4-$CH_3$ | $CH_3$ | $CH_3$ | $CH_3$ | $CH_3$ | O | $C_2H_5$ | oil |
| I-A-c-11 | H | $CH_3$ | 5-(3-Cl—$C_6H_4$) | H | $CH_3$ | $CH_3$ | $CH_3$ | $CH_3$ | O | $C_2H_5$ | |
| I-A-c-12 | H | $CH_3$ | 5-Br | H | $CH_3$ | $CH_3$ | $CH_3$ | $CH_3$ | O | $C_2H_5$ | oil |

Example II-1

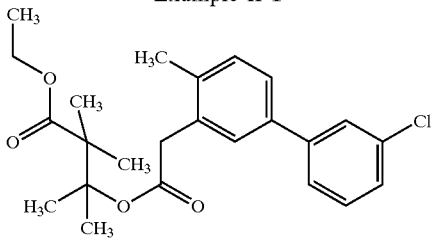

Preparation of the Acyl Chloride:

9.0 g (34.5 mmol) of 2-methyl-5-(4-chlorophenyl)-phenylacetic acid are initially charged in 50 ml of anhydrous toluene and 2 drops of DMF, and 6.15 g (51.8 mmol; 3.74 ml) of thionyl chloride are added. The mixture is stirred at 100° C. until evolution of gas has ceased. The solvent is distilled off.

6.00 g (34.5 mmol) of ethyl 3-hydroxy-2,2,3-trimethyl-butyrate and 10.3 g (34.5 mmol) of acyl chloride in 40 ml of anhydrous toluene are boiled at reflux overnight. The solvent is then distilled off and the reaction mixture is purified by silica gel column chromatography (petroleum ether:ethyl acetate. 3:1•1:1).

Yield: 11.6 g (≙80.6% of theory).

$^1$H-NMR (DMSO, 400 MHz): δ=1.06 (s, 6H, 2$CH_3$), 1.12 (t, 3H, $CO_2CH_2CH_3$), 1.50 (s, 6H, 2$CH_3$), 2.26 (s, 3H, Ar—$CH_3$), 3.66 (s, 2H, $CH_2$), 4.00 (q, 2H, $CO_2CH_2CH_3$) ppm.

The following compounds of the formula (II) are obtained analogously to Example II-1 and in accordance with the general statements on the preparation $$\text{(II)}$$

Structure: Phenyl ring with substituents X, Y, Z, W, connected via CH$_2$-C(=O)-O-C(Q$^1$)(Q$^2$)-C(A)(B)-CO$_2$R$^8$

| Ex. No. | W | X | Y | Z | B | A | Q$^1$ | Q$^2$ | R$^8$ | m.p. ° C. |
|---|---|---|---|---|---|---|---|---|---|---|
| II-2 | CH$_3$ | CH$_3$ | 4-CH$_3$ | H | CH$_2$—CCH$_3$—(CH$_2$)$_2$ | | | H | C$_2$H$_5$ | oil |
| II-3 | CH$_3$ | CH$_3$ | 4-CH$_3$ | H | CH$_3$ | CH$_3$ | CH$_3$ | CH$_3$ | C$_2$H$_5$ | oil |
| II-4 | CH$_3$ | CH$_3$ | 4-CH$_3$ | H | CH$_3$ | CH$_3$ | H | H | CH$_3$ | oil |
| II-5 | H | CH$_3$ | 5-(4-Cl—C$_6$H$_4$) | H | CH$_3$ | CH$_3$ | H | H | CH$_3$ | oil |
| II-6 | H | CH$_3$ | 5-(4-Cl—C$_6$H$_4$) | H | CH$_3$ | CH$_3$ | CH$_3$ | CH$_3$ | C$_2$H$_5$ | oil |
| II-7 | CH$_3$ | CH$_3$ | 4-(4-Cl—C$_6$H$_4$) | H | CH$_3$ | CH$_3$ | H | H | CH$_3$ | oil |
| II-8 | CH$_3$ | CH$_3$ | 4-(4-Cl—C$_6$H$_4$) | H | CH$_3$ | CH$_3$ | CH$_3$ | CH$_3$ | C$_2$H$_5$ | oil |
| II-9 | H | CH$_3$ | 5-(3-Cl—C$_6$H$_4$) | H | CH$_3$ | CH$_3$ | CH$_3$ | CH$_3$ | C$_2$H$_5$ | oil |
| II-10 | H | CH$_3$ | 5-(4-Cl—C$_6$H$_4$) | 4-CH$_3$ | CH$_3$ | CH$_3$ | CH$_3$ | CH$_3$ | C$_2$H$_5$ | oil |
| II-11 | CH$_3$ | CH$_3$ | 5-(4-Cl—C$_6$H$_4$) | 4-CH$_3$ | CH$_3$ | CH$_3$ | CH$_3$ | CH$_3$ | C$_2$H$_5$ | oil |
| II-12 | H | CH$_3$ | 5-Br | H | CH$_3$ | CH$_3$ | CH$_3$ | CH$_3$ | C$_2$H$_5$ | oil |
| II-13 | H | CH$_3$ | 5-(3,5-Cl$_2$—C$_6$H$_3$) | H | CH$_3$ | CH$_3$ | CH$_3$ | CH$_3$ | C$_2$H$_5$ | oil |
| II-14 | H | CF$_3$ | 4-Cl | H | CH$_3$ | CH$_3$ | CH$_3$ | CH$_3$ | C$_2$H$_5$ | oil |
| II-15 | Br | C$_3$H$_7$ | 4-Br | H | CH$_3$ | CH$_3$ | CH$_3$ | CH$_3$ | C$_2$H$_5$ | oil |
| II-16 | C$_2$H$_5$ | C$_2$H$_5$ | 4-Br | H | CH$_3$ | CH$_3$ | CH$_3$ | CH$_3$ | C$_2$H$_5$ | oil |
| II-17 | Cl | Cl | 4-CF$_3$ | H | CH$_3$ | CH$_3$ | CH$_3$ | CH$_3$ | C$_2$H$_5$ | oil |
| II-18 | Cl | Cl | 4-Cl | H | CH$_3$ | CH$_3$ | CH$_3$ | CH$_3$ | C$_2$H$_5$ | oil |
| II-19 | H | Cl | 5-(4-Cl—C$_6$H$_4$) | H | CH$_3$ | CH$_3$ | CH$_3$ | CH$_3$ | C$_2$H$_5$ | oil |

The compounds were obtained as oils and used without further purification for preparing compounds of the formula (I-a).

USE EXAMPLES

Example A

*Meloidogyne* Test

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal action in % is determined using the formation of galls as a measure. 100% means that no galls have been found; 0% means that the number of galls on the treated plants corresponds to that on the untreated control.

In this test, for example, the following compounds of the Preparation Examples exhibit good activity.

TABLE A

| | Plant-damaging nematodes Meloidogyne test | |
|---|---|---|
| Active compounds | Active compound concentration in ppm | Kill rate in % after 14$^d$ |
| Ex. I-a-5 | 20 | 100 |
| Ex. I-B-b-17 | 20 | 90 |
| Ex. I-B-c-1 | 20 | 90 |
| Ex. I-A-b-4 | 20 | 90 |
| Ex. I-B-c-2 | 20 | 100 |
| Ex. I-A-b-10 | 20 | 100 |
| Ex. I-A-b-1 | 20 | 100 |

Example B

*Myzus* Test

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) which are heavily infested by the peach aphid (*Myzus persicae*) are treated by being dipped into a preparation of active compound of the desired concentration.

After the desired period of time, the kill in % is determined. 100% means that all of the aphids have been killed: 0% means that none of the aphids has been killed.

In this test, for example, the following compounds of the Preparation Examples show good activity.

TABLE B

Plant-damaging insects

Myzus test

| Active compounds | Active compound concentration in ppm | Kill rate in % after 6$^d$ |
|---|---|---|
| Ex. I-a-5 | 1000 | 95 |
| Ex. I-a-7 | 1000 | 90 |
| Ex. I-a-6 | 1000 | 95 |

Example C

*Panonychus* Test

Solvent: 3 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Plum trees (*Prunus domestica*), of a height of approximately 30 cm, which are heavily infested by all stages of the fruit tree red spider mite (*Panonychus ulmi*) are sprayed with a preparation of active compound of the desired concentration.

After the desired period of time, the effect in % is determined. 100% means that all of the spider mites have been killed; 0% means that none of the spider mites has been killed.

In this test, for example, the following compound of the Preparation Examples shows good activity.

TABLE C

| | Plant-damaging mites Panonychus test | |
|---|---|---|
| Active compounds | Active compound concentration in ppm | Kill rate in % after 14$^d$ |
| Ex. I-a-6 | 200 | 100 |

Example D

*Phaedon* larvae Test

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all of the beetle larvae have been killed. 0% means that none of the beetle larvae has been killed.

In this test, for example, the following compounds of the Preparation Examples show good activity.

TABLE D

| | Plant-damaging insects | |
|---|---|---|
| | *Phaedon larvae* test | |
| Active compounds | Active compound concentration in ppm | Kill rate in % after 7$^d$ |
| Ex. I-a-5 | 1000 | 100 |
| Ex. I-a-6 | 1000 | 100 |
| Ex. I-A-b-10 | 1000 | 100 |

TABLE D-continued

| | Plant-damaging insects | |
|---|---|---|
| | *Phaedon larvae* test | |
| Active compounds | Active compound concentration in ppm | Kill rate in % after 7$^d$ |
| Ex. I-A-c-3 | 1000 | 90 |
| Ex. I-a-13 | 1000 | 100 |
| Ex. I-a-1 | 1000 | 100 |
| Ex. I-A-b-11 | 1000 | 100 |

Example E

*Spodoptera frugiperda* Test

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all of the caterpillars have been killed; 0%. means that none of the caterpillars has been killed.

In this test, for example, the following compounds of the Preparation Examples show good activity.

TABLE E

| | Plant-damaging insects *Spodoptera frugiperda* test | |
|---|---|---|
| Active compounds | Active compound concentration in ppm | Kill rate in % after 7$^d$ |
| Ex. I-a-6 | 1000 | 100 |
| Ex. I-A-b-10 | 1000 | 100 |

Example F

*Tetranychus* Test (OP-Resistant/Dip Treatment)

Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all of the spider mites have been killed, 0% means that none of the spider mites has been killed.

In this test, for example, the following compounds of the Preparation Examples show an activity which is superior to the prior art.

In this test, for example, the following compounds of the Preparation Examples show good activity.

TABLE F

Plant-damaging mites

Tetranychus test (OP-resistant/dip treatment)

| Active compounds | Active compound concentration in ppm | Kill rate in % after 7$^d$ |
| --- | --- | --- |
| Ex. I-a-6 | 100 | 100 |
| Ex. I-B-b-17 | 100 | 100 |
| Ex. I-B-c-1 | 100 | 100 |
| Ex. I-B-c-2 | 100 | 99 |
| Ex. I-B-b-16 | 100 | 100 |
| Ex. I-A-c-3 | 0.01 | 100 |

Example G

*Meloidogyne* Test

Solvent: 8 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with water to the desired concentration.

Containers are filled with sand, solution of active compound. *Meloidogyne incognita* egg/larvae suspension and lettuce seeds. The lettuce seeds germinate and the plants develop. On the roots, galls are formed.

After the desired period of time, the nematicidal action in % is determined using the formation of galls as a measure. 100% means that no galls have been found; 0% means that the number of galls on the treated plants corresponds to that on the untreated control.

Active compounds, application rates and results are shown in the table below:

TABLE G

| Nematicides *Meloidogyne incoginita* | |
| --- | --- |
| Active compound | Kill rate in % at active compound concentration in ppm |
| Ex. I-a-7 | 20 ppm = 100% |

Example H

*Sphaerotheca* Test (Cucumber)/Protective

Solvent: 48.8 parts by weight of N,N-dimethylformamide

Emulsifier: 1.2 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young cucumber plants are sprayed with the preparation of active compound at the stated application rate. 1 day after the treatment, the plants are inoculated with a spore suspension of *Sphaerotheca fuliginea*. The plants are then placed in a greenhouse at 70% relative atmospheric humidity and a temperature of 23° C.

Evaluation is carried out 7 days after the inoculation. 0% means an efficacy which corresponds to that of the control, whereas an efficacy of 100% meais that no infection is observed.

TABLE H

Sphaerotheca test (cucumber)/protective

| Active compound | Application rate of active compound in g/ha | Efficacy in % |
| --- | --- | --- |
| Ex. I-B-b-13 | 750 | 70 |
| Ex. I-A-b-3 | 750 | 80 |

Example I

Critical Concentration Test/Soil Insects—Treatment of Transgenic Plants

| Test insect: | *Diabrotica balteata* - larvae in soil |
| --- | --- |
| Solvent: | 7 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually irrelevant, only the amount by weight of active compound per volume unit of soil, which is stated in ppm (mg/l), matters. The soil is filled into 0.25 l pots and these are allowed to stand at 20° C.

Immediately after preparation, 5 pre-germinated maize corns of the variety YIELD GUARD (trademark of Monsanto Comp., USA) are placed into each pot. After 2 days, the test insects in question are placed into the treated soil. After a further 7 days, the efficacy of the active compound is determined by counting the maize plants that have emerged (1 plant=20% efficacy).

Example J

*Heliothis virescens* Test—Treatment of Transgenic Plants

| Solvent: | 7 parts by weight of acetone |
| --- | --- |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the variety Roundup Ready (tradename of Monsanto Comp. USA) are treated by being dipped into the preparation of active compound of the desired concentration and are populated with the tobacco budworm Heliothis virescens while the leaves are still moist.

After the desired period of time, the kill of the insects is determined.

What is claimed is:

1. A compound of the formula (1)

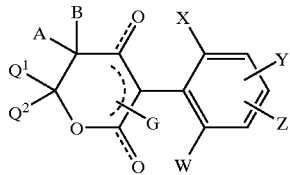 (I)

in which

W represents hydrogen, alkyl, alkenyl, alkynyl, halogen, halogenoalkyl, or alkoxy, X represents halogen, alkyl, alkoxy, alkenyl, alkynyl, halogenoalkyl, halogeno-alkoxy, or cyano; or optionally substituted phenyl, phenoxy, phenylthio, phenylalkoxy, or phenylalkylthio, Y represents hydrogen, alkyl, halogen, halogenoalkyl, alkoxy, alkenyl, alkynyl, or optionally substituted aryl, Z represents hydrogen, halogen, alkyl, alkoxy, halogenoalkyl, halogenoalkoxy, or cyano, A represents a direct bond; hydrogen; optionally halogen-substituted alkyl, alkenyl, or alkoxyalkyl; optionally substituted cycloalkyl or cycloalkylalkyl; or optionally halogen-, alkyl-, halogenoalkyl-, alkoxy-, halogenoalkoxy-, cyano- or nitro-substituted aryl, or arylalkyl, B represents hydrogen or alkyl, $Q^1$ represents hydrogen, hydroxyl, alkyl, alkoxy, alkoxyalkyl, alkylacyloxy, optionally substituted cycloalkyl, or optionally substituted phenyl, $Q^2$ represents hydrogen or alkyl, and G represents hydrogen (a) or one of the groups

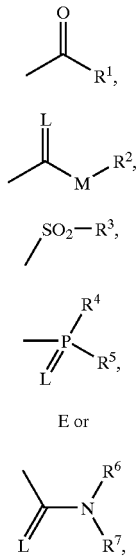

in which

E represents a metal ion or an ammonium ion,

L represents oxygen or sulphur,

M represents oxygen or sulphur, $R^1$ represents optionally halogen-substituted alkyl, alkenyl, alkoxyalkyl, alkylthioalkyl, or polyalkoxyalkyl; or optionally halogen-, alkyl-, or alkoxy-substituted cycloalkyl; or optionally substituted phenyl, phenylalkyl, or phenoxyalkyl, $R^2$ represents optionally halogen-substituted alkyl, alkenyl, alkoxyalkyl, or polyalkoxyalkyl; or optionally substituted cycloalkyl, phenyl, or benzyl, $R^3$, $R^4$, and $R^5$ independently of one another each represent optionally halogen-substituted alkyl, alkoxy, alkylamino, dialkylamino, alkylthio, alkenylthio, or cycloalkylthio; or optionally substituted phenyl, benzyl, phenoxy, or phenylthio, and $R^6$ and $R^7$ independently of one another each represent hydrogen; optionally halogen-substituted alkyl, cycloalkyl, alkenyl, alkoxy, or alkoxyalkyl; optionally substituted phenyl; or optionally benzyl.

2. A compound of the formula (1) according to claim 1 in which

W represents hydrogen, $C_1$–$C_6$-alkyl, $C_2$–$C_4$-alkenyl, ethynyl, fluorine, chlorine, bromine, $C_1$–$C_4$-halogenoalkyl, or $C_1$–$C_6$-alkoxy, X represents fluorine, chlorine, bromine, $C_1$–$C_6$-alkyl, $C_1$–$C_4$-halogenoalkyl, $C_1$–$C_6$-alkoxy, $C_2$–$C_4$-alkenyl, ethynyl, $C_1$–$C_4$-halogenoalkoxy, or cyano; or optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, nitro-, or cyano-substituted phenyl or benzyloxy, Y represents hydrogen, $C_1$–$C_6$-alkyl, $C_1$–$C_4$-halogenoalkyl, fluorine, chlorine, bromine, $C_1$–$C_6$-alkoxy, $C_2$–$C_4$-alkenyl, or ethynyl; or represents

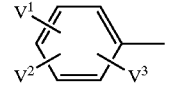

in which

V1 represents hydrogen, halogen, $C_1$–$C_{12}$-alkyl, 1–$C_6$-alkoxy, $C_1$–$C_6$-alkylthio, $C_1$–$C_4$-halogenoalkyl, $C_1$–$C_4$-halogenoalkoxy, nitro, or cyano; or phenyl, phenoxy, phenoxy-$C_1$–$C_4$-alkyl, phenyl-$C_1$–$C_4$-alkoxy, phenylthio-$C_1$–$C_4$-alkyl, or phenyl-$C_1$–$C_4$-alkylthio, each of which is optionally mono- or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro, or cyano, V2 represents hydrogen, fluorine, chlorine, $C_1$–$C_6$-alkyl, $C_1$–$C_6$-alkoxy, $C_1$–$C_4$-halogenoalkyl, or $C_1$–$C_4$-halogenoalkoxy, and V3 represents hydrogen, fluorine, chlorine, methyl, or methoxy, Z represents hydrogen, fluorine, chlorine, bromine, $C_1$–$C_6$-alkyl, $C_1$–$C_4$-halogenoalkyl, $C_1$–$C_6$-alkoxy, $C_1$–$C_4$-halogenoalkoxy, or cyano, with the provisos that (i) W, X, and Z do not represent bromine, $C_2$–$C_4$-alkenyl, and ethynyl if Y represents V1, V2-, and V3-substituted phenyl and (ii) no more than two of the radicals W, X, and Y represent $C_2$–$C_4$-alkenyl or ethynyl, and (iii) none of the other radicals W, X, Y, and Z may represent bromine, A represents a direct bond; hydrogen; optionally halogen-substituted $C_1$–$C_{12}$-alkyl, $C_3$–$C_8$-alkenyl, or $C_1$–$C_6$-alkoxy-$C_1$–$C_4$-alkyl; optionally halogen-, $C_1$–$C_4$-alkyl- or $C_1$–$C_4$-alkoxy-substituted $C_3$–$C_8$-cycloalkyl or $C_3$–$C_6$-cycloalkyl-$C_1$–$C_4$-alkyl; or optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano-, or nitro-substituted phenyl, or benzyl, B represents hydrogen or $C_1$–$C_6$-alkyl, $Q^1$ represents hydrogen, hydroxyl, $C_1$–$C_6$-alkyl, $C_1$–$C_6$-alkoxy, $C_1$–$C_6$-alkoxy-$C_1$–$C_2$-alkyl, or $C_1$–$C_6$- alkylacyloxy; optionally fluorine-, chlorine-, $C_1$–$C_4$-alkyl-, $C_1$–$C_2$-halogenoalkyl-, or $C_1$–$C_4$-alkoxy-substituted $C_3$–$C_8$-cycloalkyl; or optionally halogen, $C_1$–$C_4$-alkyl-, $C_1$–$C_4$-alkoxy-, $C_1$–$C_2$-halogenoalkyl-, $C_1$–$C_2$-halogenoalkoxy-, cyano-, or nitro-substituted phenyl, $Q^2$ represents hydrogen or $C_1$–$C_4$-alkyl, and G represents hydrogen (a) or one of the groups

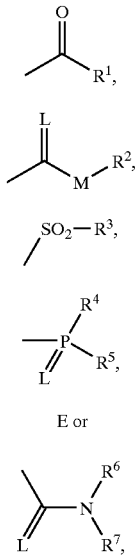

(b)
(c)
(d)
(e)
(f) E or
(g)

in which

E represents a metal ion or an ammonium ion,

L represents oxygen or sulphur,

M represents oxygen or sulphur, $R^1$ represents optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, or poly-$C_1$–$C_8$-alkoxy-$C_1$–$C_8$-alkyl; optionally halogen-, $C_1$–$C_6$-alkyl-, or $C_1$–$C_6$-alkoxy-substituted $C_3$–$C_8$-cycloalkyl; optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio-, or $C_1$–$C_6$-alkylsulphonyl-substituted phenyl; optionally halogen-, nitro-, cyano-, $C_1$–$C_6$-alkyl-, $C_1$–$C_6$-alkoxy-, $C_1$–$C_6$-halogenoalkyl-, or $C_1$–$C_6$-halogenoalkoxy-substituted phenyl-$C_1$–$C_6$-alkyl; optionally halogen- or $C_1$–$C_6$-alkyl-substituted phenoxy-$C_1$–$C_6$-alkyl;

$R^2$ represents optionally halogen-substituted $C_1$–$C_{20}$-alkyl, $C_2$–$C_{20}$-alkenyl, $C_1$–$C_8$-alkoxy-$C_2$–$C_8$-alkyl, or poly-$C_1$–$C_8$-alkoxy-$C_2$–$C_8$-alkyl; optionally halogen-, $C_1$–$C_6$-alkyl-, or $C_1$–$C_6$-alkoxy-substituted $C_3$–$C_8$-cycloalkyl; or optionally halogen-, cyano-, nitro-, $C_1$–$C_6$-alkyl-, $C_1$–$C_6$-alkoxy-, $C_1$–$C_6$-halogenoalkyl-, or $C_1$–$C_6$-halogenoalkoxy-substituted phenyl or benzyl, $R^3$ represents optionally halogen-substituted $C_1$–$C_8$-alkyl; or optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano-, or nitro-substituted phenyl or benzyl, $R^4$ and $R^5$ independently of one another each represent optionally halogen-substituted $C_1$–$C_8$-alkyl, $C_1$–$C_8$-alkoxy, $C_1$–$C_8$-alkylamino, di($C_1$–$C_8$-alkyl)amino, $C_1$–$C_8$-alkylthio, $C_2$–$C_8$-alkenylthio, or $C_3$–$C_8$-cycloalkylthio; or optionally halogen-, nitro-, cyano-, $C_1$–$C_4$-alkoxy-, $C_1$–$C_4$-halogeno-alkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, benzyl, phenoxy, or phenylthio, and $R^6$ and $R^7$ independently of one another each represent hydrogen; optionally halogen-substituted $C_1$–$C_8$-alkyl, $C_3$–$C_8$-cycloalkyl, $C_1$–$C_8$-alkoxy, $C_3$–$C_8$-alkenyl, or $C_1$–$C_8$-alkoxy-$C_1$–$C_8$-alkyl; optionally halogen-, $C_1$–C8-halogenoalkyl-, $C_1$–$C_8$-alkyl-, or $C_1$–$C_8$-alkoxy-substituted phenyl; or optionally halogen-, $C_1$–$C_8$-alkyl-, $C_1$–$C_8$-halogenoalkyl-, or $C_1$–$C_8$-alkoxy-substituted benzyl.

3. A compound of the formula (1) according to claim 1 in which

W represents hydrogen, $C_1$–$C_4$-alkyl, chlorine, or bromine,

X represents chlorine, bromine, $C_1$–$C_4$-alkyl, $C_1$–$C_4$-alkoxy, $C_2$–$C_3$-alkenyl, ethynyl, $C_1$–$C_2$-halogenoalkyl, $C_1$–$C_2$-halogenoalkoxy, or cyano, Y represents hydrogen, $C_1$–$C_4$-alkyl, $C_1$–$C_2$-halogenoalkyl, fluorine, chlorine, bromine, $C_1$–$C_4$-alkoxy, $C_2$–$C_3$-alkenyl, or ethynyl; or represents the radical

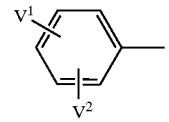

in which

V1 represents hydrogen, fluorine, chlorine, bromine, $C_1$–$C_6$-alkyl, $C_1$–$C_4$-alkoxy, $C_1$–C4-alkylthio, $C_1$–$C_2$-halogenoalkyl, $C_1$–$C_2$-halogenoalkoxy, nitro, cyano, or phenyl and V2 represents hydrogen, fluorine, chlorine, $C_1$–$C_4$-alkyl, $C_1$–$C_4$-alkoxy, or $C_1$–$C_2$-halogenoalkyl, Z represents hydrogen, fluorine, chlorine, bromine, $C_1$–$C_4$-alkyl, $C_1$–$C_4$-alkoxy, $C_1$–C2-halogenoalkyl, or $C_1$–$C_2$-halogenoalkoxy, with the provisos that (i) W, X, and Z do not represent bromine, $C_2$–$C_3$alkenyl, and ethynyl if Y represents V1- and V2-substituted phenyl, (ii) only one of the radicals X and Y represents $C_2$–$C_3$-alkenyl and ethynyl, and (iii) none of the other radicals W, X, Y, and Z may represent bromine, A represents a direct bond; hydrogen; optionally fluorine-substituted $C_1$–$C_8$-alkyl, or $C_1$–$C_4$-alkoxy-$C_1$–$C_2$-alkyl; optionally fluorine-, chlorine-, methyl-, ethyl-, or methoxy-substituted $C_5$–$C_6$-cycloalkyl or $C_5$–$C_6$-cycloalkyl-$C_1$–$C_2$-alkyl; or optionally fluorine-, chlorine-, bromine-, $C_1$–$C_4$-alkyl-, $C_1$–$C_2$-halogenoalkyl-, $C_1$–$C_4$-alkoxy-, or $C_1$–$C_2$-halogenoalkoxy-substituted phenyl or benzyl, B represents hydrogen or $C_1$–$C_4$-alkyl, $Q^1$ represents hydrogen, hydroxyl, $C_1$–$C_4$-alkyl, $C_1$–$C_4$-alkoxy, $C_1$–$C_4$-alkoxy-C1–$C_2$-alkyl, or $C_1$-alkylacyloxy; or optionally methyl- or methoxy-substituted $C_3$–$C_6$-cycloalkyl, $Q^2$ represents hydrogen, methyl, or ethyl, and G represents hydrogen (a) or one of the groups

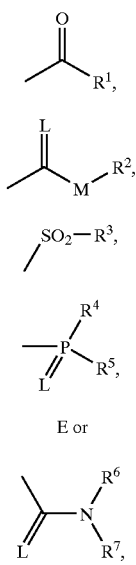

E or in which

E represents a metal ion or an ammonium ion,

L represents oxygen or sulphur,

M represents oxygen or sulphur, $R^1$ represents optionally fluorine- or chlorine-substituted $C_1$–$C_{16}$-alkyl, $C_2$–$C_{16}$-alkenyl, $C_1$–$C_4$-alkoxy-$C_1$–$C_2$-alkyl, or $C_1$–$C_4$-alkylthio-C1–$C_2$-alkyl; or optionally fluorine-, chlorine-, $C_1$–$C_2$-alkyl-, or $C_1$–$C_2$-alkoxy-substituted 3-$C_7$-cycloalkyl; or phenyl that is optionally mono- or disubstituted by fluorine, chlorine, bromine, cyano, nitro, $C_1$–$C_4$-alkyl, $C_1$–$C_4$-alkoxy, trifluoromethyl, or trifluoromethoxy;

$R^2$ represents $C_1$–$C_{16}$-alkyl, $C_2$–$C_{16}$-alkenyl, or $C_1$–$C_4$-alkoxy-$C_2$–$C_4$-alkyl, each of which is optionally mono- to trisubstituted by fluorine; $C_3$–$C_7$-cycloalkyl that is optionally monosubstituted by methyl, ethyl, or Methoxy; or phenyl or benzyl, each of which is optionally mono- or disubstituted by fluorine, chlorine bromine, cyano, nitro, $C_1$–$C_4$-alkyl, $C_1$–$C_3$-alkoxy, trifluoromethyl, or trifluoromethoxy, $R^3$ represents $C_1$–$C_6$-alkyl that is optionally mono- to pentasubstituted by fluorine; or phenyl that is optionally mono- or disubstituted by fluorine, chlorine, bromine, $C_1$–$C_4$-alkyl, $C_1$–$C_4$-alkoxy, trifluoromethyl, trifluoro-methoxy, cyano, or nitro, $R^4$ represents $C_1$–$C_6$-alkyl, $C_1$–$C_6$-alkoxy, $C_1$–$C_6$-alkylamino, di($C_1$–$C_6$-alkylamino, or $C_1$–$C_6$-alkylthio; or phenyl, benzyl, phenoxy, or phenylthio, each of which is optionally mono- or disubstituted by fluorine, chlorine, bromine, nitro, cyano, $C_1$–$C_3$-alkoxy, trifluoro-methoxy, $C_1$–$C_3$-alkyl, or trifluoromethyl, $R^5$ represents $C_1$–$C_4$-alkyl, $C_1$–$C_4$-alkoxy, or $C_1$–$C_4$-alkylthio, $R^6$ represents $C_1$–$C_6$-alkyl, $C_3$–$C_6$-cycloalkyl, $C_1$–$C_6$-alkoxy, $C_3$–$C_6$-alkenyl, or $C_1$–$C_6$-alkoxy-$C_1$–$C_6$-alkyl; phenyl that is optionally mono- or disubstituted by fluorine, chlorine, bromine, trifluoromethyl, $C_1$–$C_4$-alkyl, or $C_1$–$C_4$-alkoxy, or benzyl that is optionally mono- or disubstituted by fluorine, chlorine, bromine, methyl, ethyl, trifluoromethyl, or methoxy, and $R^7$ represents hydrogen, $C_1$–$C_6$-alkyl, or $C_3$–$C_6$-alkenyl.

4. A compound of the formula (1) according to claim 1 in which

W represents hydrogen, chlorine, bromine, methyl, or ethyl,

X represents chlorine, bromine, methyl, ethyl, n-propyl, methoxy, ethoxy, trifluoromethyl, difluoromethoxy, trifluoromethoxy, or cyano, Y represents hydrogen, methyl, ethyl, propyl, iso-propyl, fluorine, chlorine, bromine, or methoxy; or represents the radical

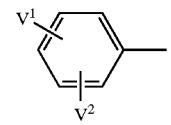

in which

V1 represents hydrogen, fluorine, chlorine, bromine, methyl, ethyl, iso-propyl, tert-butyl, methoxy, trifluoromethyl or trifluoromethoxy, cyano, or phenyl, and V2 represents hydrogen, fluorine, chlorine, methyl, methoxy, or trifluoromethyl, Z represents hydrogen, fluorine, chlorine, bromine, methyl, methoxy, or trifluoromethyl, with the proviso that W, X, and Z do not represent bromine if Y represents V1- and V2-substituted phenyl, A represents a direct bond, hydrogen, methyl, ethyl, n-propyl, iso-propyl, n-butyl, or iso-butyl, B represents hydrogen, methyl, or ethyl, $Q^1$ represents hydrogen, hydroxyl, methyl, ethyl, n-propyl, iso-propyl, methoxy, ethoxy, propoxy, acetyloxy, or propionyloxy, $Q^2$ represents hydrogen, methyl, or ethyl, and G represents hydrogen (a) or one of the groups

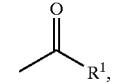

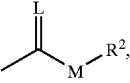

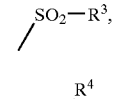

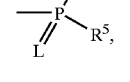

E or

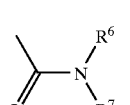

in which

E represents a metal ion or an ammonium ion,

L represents oxygen or sulphur,

M represents oxygen or sulphur, $R^1$ represents optionally fluorine- or chlorine-substituted $C_1$–$C_8$-alkyl, $C_2$–$C_8$-alkenyl, $C_1$–$C_2$-alkoxy-$C_1$-alkyl, $C_1$-alkylthio-$C_1$-alkyl, cyclopropyl, cyclopentyl, or cyclohexyl; or phenyl that is optionally monosubstituted by fluorine, chlorine, bromine, cyano, nitro, methyl, ethyl, iso-propyl, tert-butyl, methoxy, trifluoromethyl, or trifluoro-methoxy;

$R^2$ represents $C_1$–$C_8$-alkyl, $C_2$–$C_8$-alkenyl, $C_1$–$C_4$-alkoxy-$C_2$-alkyl, or cyclohexyl; or phenyl or benzyl, each of which is optionally mono-substituted by fluorine, bromine, chlorine, cyano, nitro, methyl, tert-butyl, methoxy, trifluoromethyl, or trifluoromethoxy, $R^3$ represents methyl, ethyl, n-propyl, or phenyl that is optionally mono-substituted by fluorine, chlorine, bromine, methyl, tert-butyl, methoxy, trifluoromethyl, trifluoromethoxy, cyano, or nitro, $R^4$ represents $C_1$–$C_4$-alkyl, $C_1$–$C_4$-alkoxy, $C_1$–$C_4$-alkylamino, di($C_1$–$C_4$-alkyl)amino, or $C_1$–$C_4$-alkylthio; or phenyl, phenoxy, or phenylthio, each of which is optionally monosubstituted by fluorine, chlorine, bromine, nitro, cyano, $C_1$–$C_2$-alkoxy, trifluoromethoxy, or $C_1$–$C_3$-alkyl, $R^5$ represents methyl, ethyl, methoxy, ethoxy, methylthio, or ethylthio, $R^6$ represents $C_1$–$C_4$-alkyl, $C_3$–$C_6$-cycloalkyl, $C_1$–$C_4$-alkoxy, $C_3$–$C_4$-alkenyl, or $C_1$–$C_4$-alkoxy-$C_1$–$C_4$-alkyl, and $R^7$ represents hydrogen, $C_1$–$C_4$-alkyl, or $C_3$–$C_4$-alkenyl.

5. A compound of the formula (1) according to claim 1 in which

W represents hydrogen, methyl, ethyl, chlorine, or bromine,

X represents methyl, ethyl, n-propyl, trifluoromethyl, or chlorine,

Y represents methyl, trifluoromethyl, chlorine, or bromine; or phenyl that is optionally mono- or disubstituted by chlorine and/or methyl, Z represents hydrogen or methyl, with the proviso that W does not represent bromine if Y represents substituted phenyl, A represents methyl, ethyl, or a direct bond, B represents methyl or ethyl, $Q^1$ represents hydrogen, methyl, methoxy, ethoxy, propoxy, hydroxyl, or acetyloxy, $Q^2$ represents hydrogen or methyl, and G represents hydrogen(a) or one of the groups

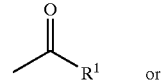 (b)

or

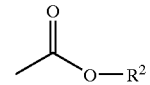 (c)

where $R^1$ represents $C_1$–$C_4$-alkyl or represents phenyl, each of which is optionally monosubstituted by chlorine, and $R^2$ represents $C_1$–$C_4$-alkyl.

6. A pesticide comprising one or more compounds of the formula (I) according to claim 1 and one or more extenders.

7. A method for controlling pests comprising allowing a pesticidally effective amount of a compound of the formula (I) according to claim 1 to act on the pests and/or their habitat.

8. A process for preparing a pesticide or herbicide comprising mixing a compound of the formula (I) according to claim 1 with one or more extenders.

* * * * *